(12) United States Patent
Hu et al.

(10) Patent No.: US 11,291,369 B2
(45) Date of Patent: Apr. 5, 2022

(54) METHOD AND APPARATUS FOR MONITORING COLLECTION OF PHYSIOLOGICAL PATIENT DATA

(71) Applicant: University Of Maryland, Baltimore, Baltimore, MD (US)

(72) Inventors: Fu-Ming Hu, Ellicott City, MD (US); Lynn G. Stansbury, Seattle, WA (US); Colin F. Mackenzie, Pasadena, MD (US); Thomas M. Scalea, Baltimore, MD (US); Deborah M. Stein, Owings Mills, MD (US); Shiming Yang, Halethorpe, MD (US)

(73) Assignee: University Of Maryland, Baltimore, Baltimore, MD (US)

( * ) Notice: Subject to any disclaimer, the term of this patent is extended or adjusted under 35 U.S.C. 154(b) by 590 days.

(21) Appl. No.: 15/976,409

(22) Filed: May 10, 2018

(65) Prior Publication Data
US 2018/0368683 A1    Dec. 27, 2018

Related U.S. Application Data

(60) Provisional application No. 62/504,891, filed on May 11, 2017.

(51) Int. Cl.
*A61B 5/00*  (2006.01)
*A61B 5/0205*  (2006.01)
(Continued)

(52) U.S. Cl.
CPC .......... *A61B 5/0022* (2013.01); *A61B 5/0006* (2013.01); *A61B 5/0008* (2013.01);
(Continued)

(58) Field of Classification Search
CPC ... A61B 5/0022; A61B 5/0006; A61B 5/0008; A61B 5/02055; A61B 5/1113; A61B 5/01; A61B 5/0002; G16H 10/40; G16H 10/60
See application file for complete search history.

(56) References Cited

U.S. PATENT DOCUMENTS

| 2015/0177063 A1* | 6/2015 | Lian | G01J 1/0403 |
| | | | 250/372 |
| 2016/0175595 A1* | 6/2016 | Lian | A61N 1/0556 |
| | | | 607/18 |

(Continued)

FOREIGN PATENT DOCUMENTS

WO    2017197120    11/2017

OTHER PUBLICATIONS

Arora, M., et al.. Evaluation of CoViSTA—an automated vital sign documentation system—in an inpatient hospital setting, "AMIA Annu. Symp. Proc.", p. 885 (2005).

(Continued)

*Primary Examiner* — Hoi C Lau
(74) *Attorney, Agent, or Firm* — Wolter Van Dyke Davis, PLLC; Eugene J. Molinelli; Cian O'Brien

(57) ABSTRACT

A method and apparatus for monitoring collection of subject condition data is provided. The method includes receiving a value of a parameter of subject condition data and a value of a sample time, for each of a plurality of sample times. The method also includes storing the subject condition data in a data structure including a first field for holding data indicating a current sample time and a second field for holding data indicating the value of the parameter. The method also includes determining a time gap defined by a duration between the current sample time and a most recent sample time and determining whether the time gap exceeds a time gap threshold and causing an apparatus to perform remedial (Continued)

action. A method for presenting the subject condition data on a display is also provided.

24 Claims, 19 Drawing Sheets

(51) Int. Cl.
  *A61B 5/11*     (2006.01)
  *A61B 5/024*    (2006.01)
  *A61B 5/01*     (2006.01)
  *A61B 5/1455*    (2006.01)
  *G16H 10/60*    (2018.01)
  *G16H 10/40*    (2018.01)

(52) U.S. Cl.
  CPC ........ *A61B 5/02055* (2013.01); *A61B 5/1113* (2013.01); *G16H 10/40* (2018.01); *G16H 10/60* (2018.01); *A61B 5/01* (2013.01); *A61B 5/02405* (2013.01); *A61B 5/1455* (2013.01)

(56) References Cited

U.S. PATENT DOCUMENTS

| | | | |
|---|---|---|---|
| 2016/0305819 A1* | 10/2016 | Lian | A61B 5/441 |
| 2017/0013547 A1* | 1/2017 | Skaaksrud | H04L 41/12 |
| 2017/0265786 A1* | 9/2017 | Fereczkowski | A61B 5/123 |
| 2018/0103913 A1* | 4/2018 | Tzvieli | G06K 9/3233 |
| 2018/0104439 A1* | 4/2018 | Tzvieli | A61B 5/0816 |
| 2018/0368683 A1* | 12/2018 | Hu | A61B 5/0022 |
| 2019/0110692 A1* | 4/2019 | Pardey | A61B 5/7275 |
| 2019/0133534 A1* | 5/2019 | Hu | A61B 5/7264 |
| 2020/0015697 A1* | 1/2020 | Kinreich | A61B 5/375 |
| 2020/0170517 A1* | 6/2020 | Addison | A61B 5/02028 |
| 2020/0338350 A1* | 10/2020 | Panken | A61B 5/7264 |
| 2020/0400816 A1* | 12/2020 | Sugae | G01S 15/04 |

OTHER PUBLICATIONS

Fieler, V., "Eliminating Errors in Vital Signs Documentation, GIN, 2013, pp. 422-427", vol. 31, No. 9.

Hu, P., et al., "Reliable Collection of Real-Time Patient Physiologic data from less reliable networks: a monitor of monitors system (MoMs)", J. Med. Syst., vol. 41, Issue 3, pp. 1-8 (2017).

Kahraman, S., et al., "Dynamic Three-Dimensional Scoring of Cerebral Perfusion Pressure and Intracranial Pressure Provides a brain trauma index that predicts outcome in patients with severe traumatic brain injury", J. of Trauma, vol. 70, Issue 3, pp. 547-553 (2011).

Mackenzie, C., et al., "Real-Time decision support during trauma patient resuscitation", Proceedings of Association of University Anesthesiologists (2011).

Sydney South West Area Health Service, Royal Prince Alfred Hospital Patient Observation (Vital Signs) Policy—Adult, "Policy Directive", pp. 1-13 (2010).

Yang, S., et al., "Real Time Vital Signs Monitor System for critical care air transport team (CCATT) A prototype design", Presentation, 18 Pages (2016).

\* cited by examiner

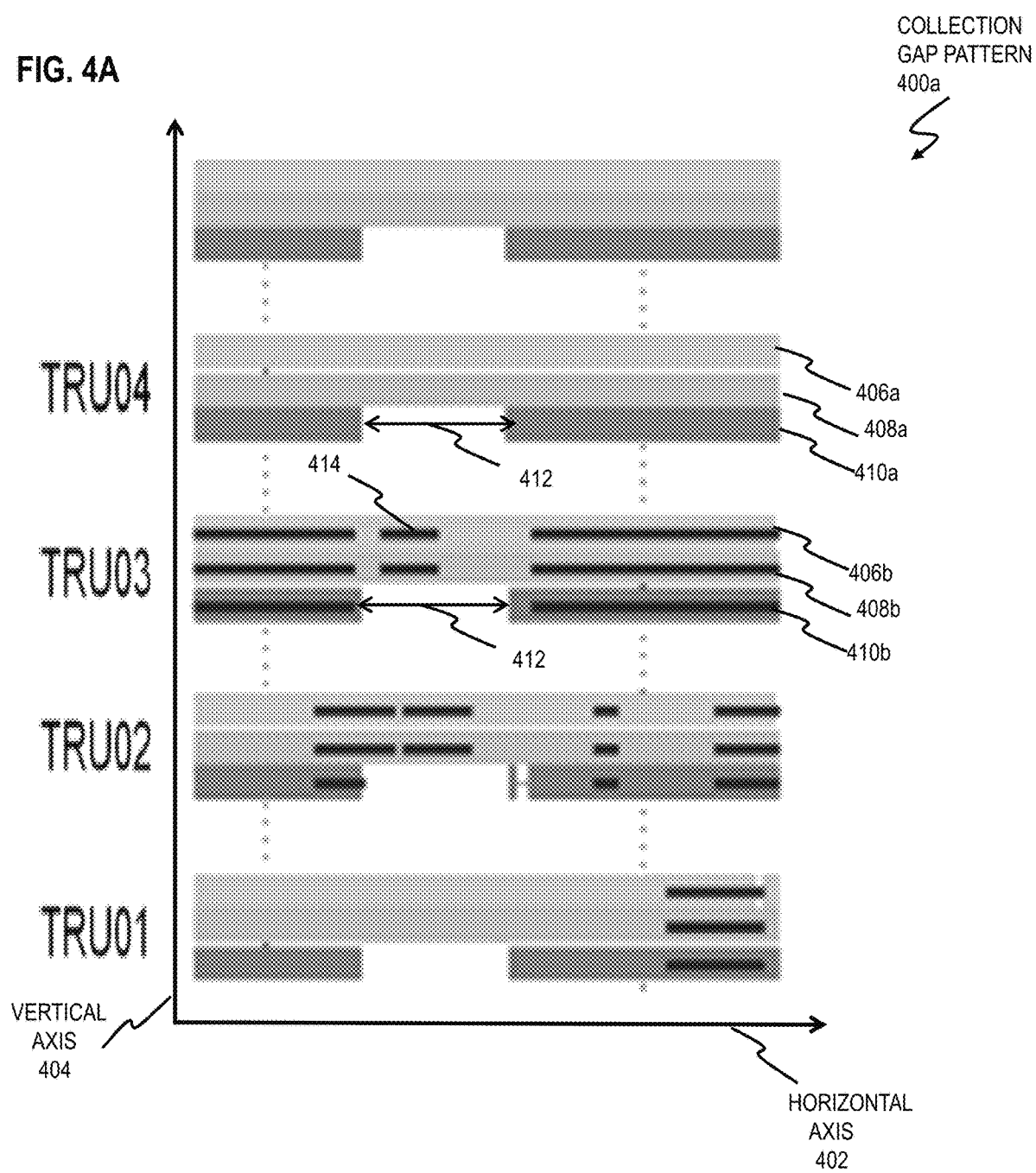

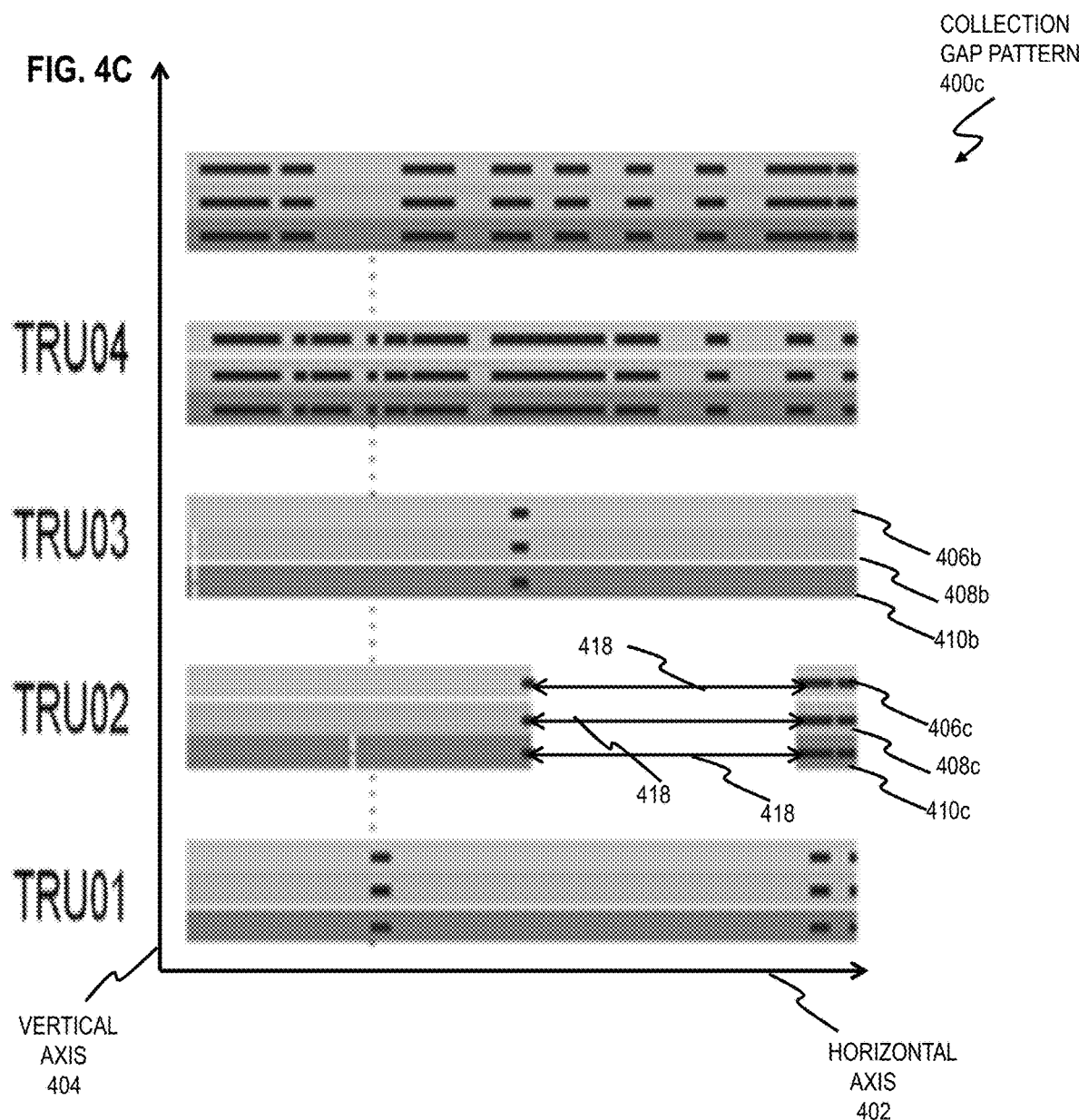

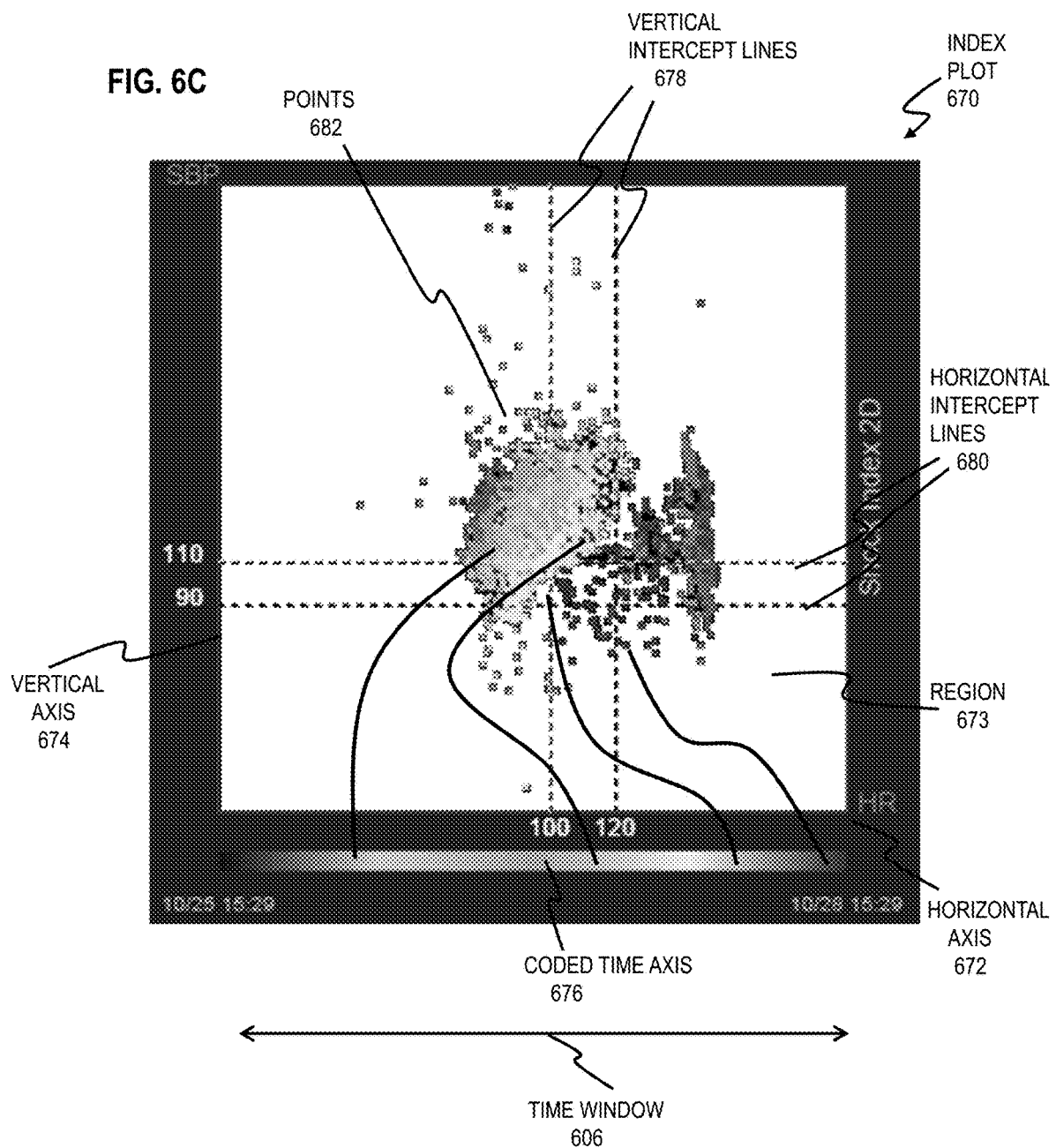

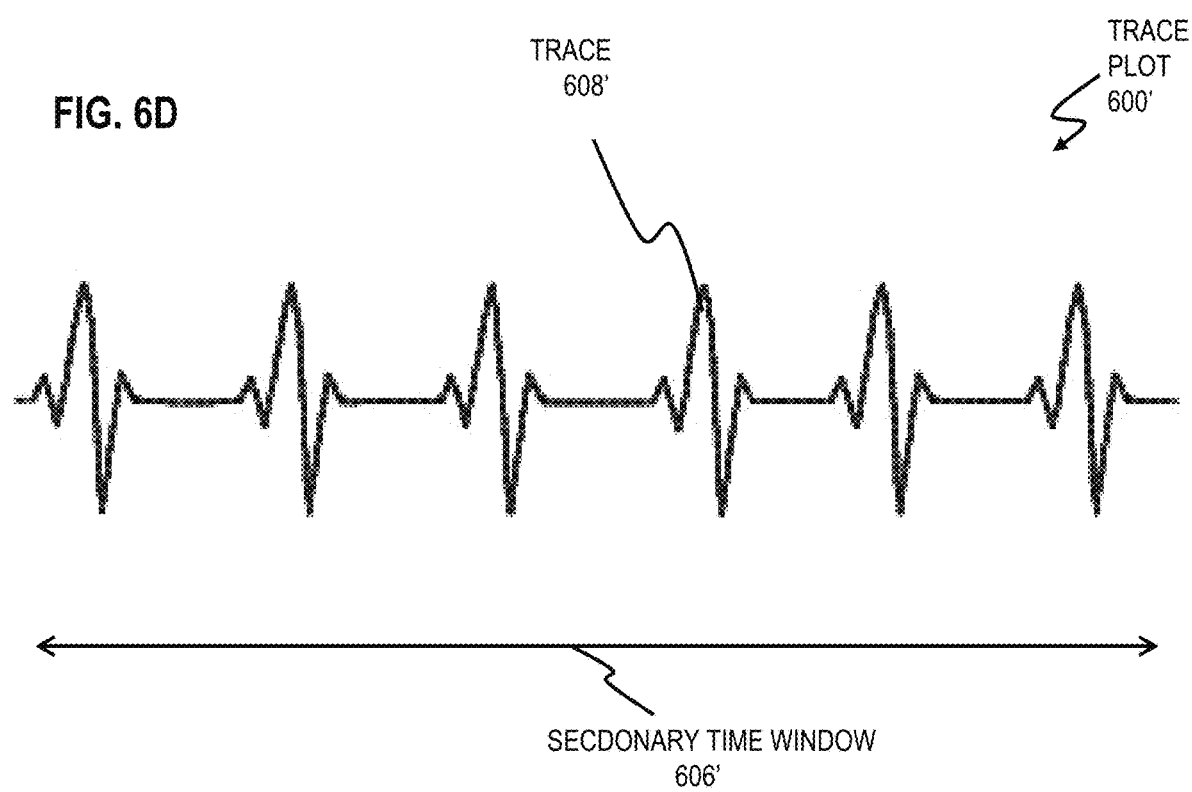

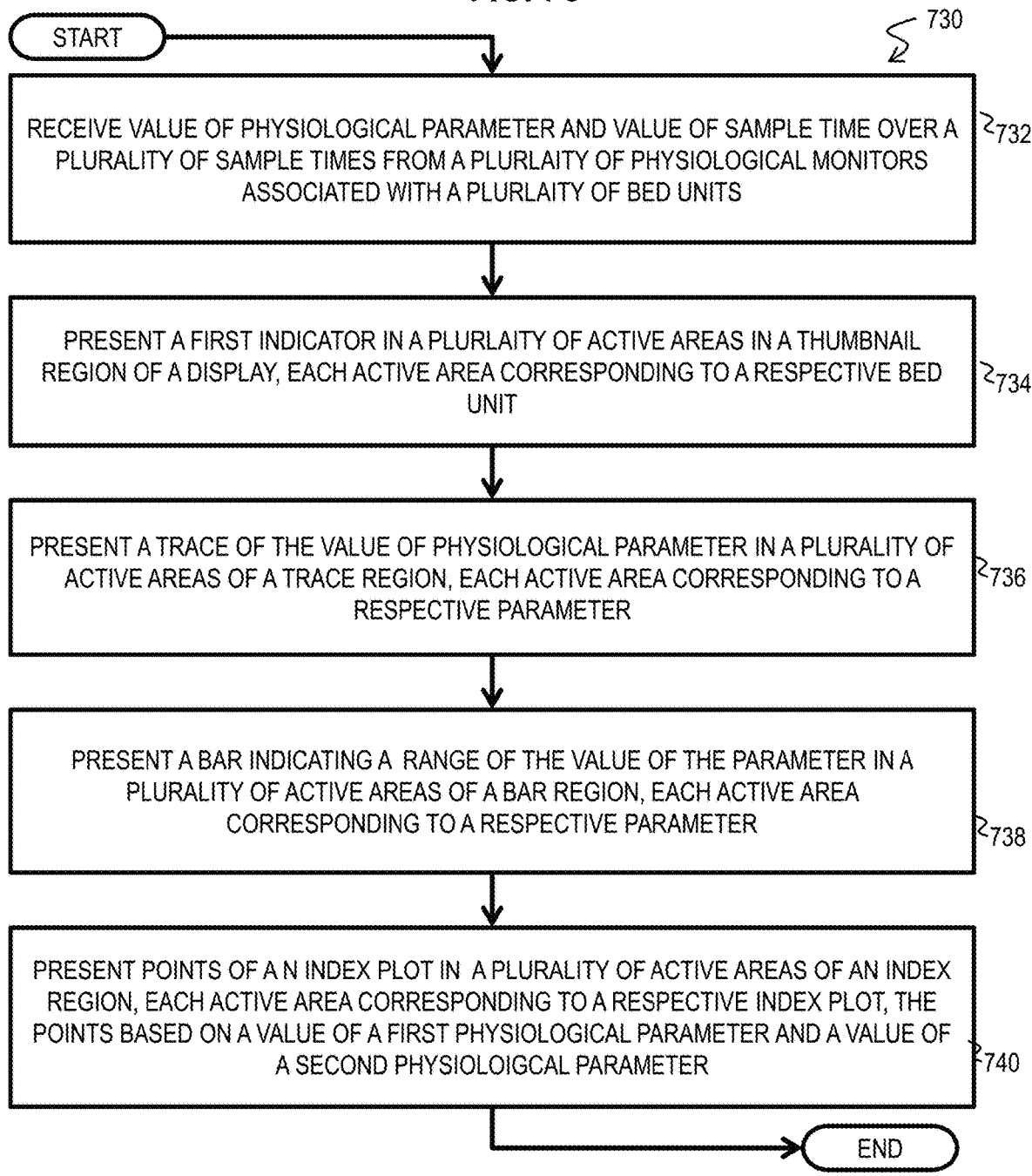

METHOD AND APPARATUS FOR MONITORING COLLECTION OF PHYSIOLOGICAL PATIENT DATA

CROSS REFERENCE TO RELATED APPLICATIONS

This application claims the benefit of provisional application 62/504,891, filed May 11, 2017, the entire contents of which are incorporated herein.

STATEMENT OF GOVERNMENTAL INTEREST

This invention was made with government support under Grant No. W81XWH-07-2-0118 awarded by the U.S. Army Medical Research and Material Command, under Grant No. IIS0534646 awarded by the National Science Foundation and under Grant No. FA8650-11-2-6D01 awarded by the Air Force Office of Scientific Research. The government has certain rights in the invention.

BACKGROUND

Automated electronic patient monitoring and data collection systems are used to collect real time physiological data over a plurality of sample times from physiological data monitors associated with units in a facility. Multiple servers receive the physiological data from the physiological data monitors. In the event that one of the servers does not record physiological data at a sample time, the system assesses whether another of the servers recorded physiological data at the sample time. If none of the servers record physiological data at the sample time, the system classifies the sample time as a time gap in the collection of physiological data. Collection performance of these systems is assessed based on a collection rate defined as a percentage of the sample times where physiological data is recorded.

SUMMARY

It is here recognized that conventional automated electronic patient monitoring and data collection systems are deficient, since they merely assess whether there is a time gap in the collection of physiological data at each sample time and do not take remedial action to diagnose and resolve the time gap. Consequently, the collection rate of conventional systems is limited. Collection rates in conventional systems range between 28% and 40% when using a single server and approximately 79% when multiple servers are connected redundantly, e.g. if one server does not record data, a backup server is relied upon to provide the recorded data. An advantage of the monitoring and data collection system described herein is that, in an experimental embodiment, the collection rate significantly improved to a range between 87% and 95% when using a single server and to 99.88% when multiple servers are connected redundantly.

In a first set of embodiments, a method is provided for monitoring collection of subject condition data. The method includes receiving a value of a parameter of subject condition data and a value of a sample time at each of a plurality of sample times from one or more servers. The value of the parameter and the value of the sample time is received on the one or more servers from a plurality of subject condition data monitors associated with a respective plurality of units in a facility. The method further includes storing the subject condition data from each unit in a data structure for a current sample time. The data structure includes a first field for holding data indicating the current sample time. The data structure also includes a second field for holding data indicating a value of the parameter of subject condition data. The method further includes determining a time gap defined by a duration between the current sample time and a most recent sample time. The method further includes determining whether the time gap for each unit exceeds one or more time gap thresholds. The method further includes causing an apparatus to perform a remedial action based on the determining step.

In a second set of embodiments, non-transitory computer-readable medium is provided for storing a sequence of instructions and a data structure including two or more records, where each record includes two or more fields. Execution of the one or more sequences of instructions by one or more processors causes the one or more processors to perform one or more steps of the above method.

In a third set of embodiments, an apparatus is provided for monitoring collection of subject condition data. The apparatus includes a processor, a memory including one or more sequences of instructions and a data structure including two or more records and where each record includes two or more fields. The memory and the sequence of instructions are configured to, with the processor, cause the apparatus to perform one or more steps of the above method.

In a fourth set of embodiments, a method is provided for displaying subject condition data relating to monitoring a plurality of subjects in a respective plurality of units of a facility, where the plurality of units are divided into one or more groups of the facility. The method includes receiving a value of a parameter of subject condition data and a value of a sample time at each of a plurality of sample times from a plurality of subject condition data monitors associated with the respective plurality of units. The method further includes presenting a first indicator in each of a first plurality of active areas in a group region of a display, where each active area in the group region corresponds to a respective group of the facility. In response to a selection of a particular active area of the group region, the method further includes presenting a representation based on the value of the parameter of subject condition data in each of a second plurality of active areas in a unit region of the display, where each active area in the unit region corresponds to a respective unit within the group corresponding to the particular active area of the group region.

In a fifth set of embodiments, a method is provided for displaying subject condition data relating to monitoring a plurality of subjects in a respective plurality of units. The method includes receiving a value of a parameter of subject condition data and a value of a sample time at each of a plurality of sample times from a plurality of subject condition data monitors associated with the respective plurality of units. The method further includes presenting a first indicator in each of a first plurality of active areas in a thumbnail region of a display, where each active area in the thumbnail region corresponds to a respective unit. The method further includes presenting a trace of the value of the parameter of subject condition data over a time window encompassed by the plurality sample times in each of a second plurality of active areas of a trace region of the display. Each active area in the trace region corresponds to a respective parameter. The method further includes presenting a bar that indicates an occurrence of the value of the parameter over the time window in each of a third plurality of active areas of a bar region of the display. Each active area in the bar region corresponds to a respective parameter. The method further includes presenting points in an index plot over the time window in at least one active area in an index region of the display. Each active area in the index region corresponds to a respective index plot, where the points are based on a value of a first parameter of subject condition data and a value of a second parameter of subject condition data.

Still other aspects, features, and advantages are readily apparent from the following detailed description, simply by illustrating a number of particular embodiments and implementations, including the best mode contemplated for carrying out the invention. Other embodiments are also capable of other and different features and advantages, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

Embodiments are illustrated by way of example, and not by way of limitation, in the figures of the accompanying drawings in which like reference numerals refer to similar elements and in which:

FIG. 4A is a graph that illustrates a first example collection gap pattern of physiological data at the plurality of servers from the plurality of physiological data monitors of FIG. 1B, according to an embodiment;

FIG. 4C is a graph that illustrates a third example collection gap pattern of physiological data at the plurality of servers from the plurality of physiological data monitors of FIG. 1B, according to an embodiment;

FIG. 6C is an image that illustrates an example of an index plot of the index region of FIG. 5B, according to an embodiment;

FIG. 6D is an image that illustrates an example of a trace of a value of a waveform parameter of physiological patient data, according to an embodiment;

FIG. 7C is a flow diagram that illustrates an example of a method for displaying a unit view of physiological data collected from a plurality of bed units in a medical facility, according to an embodiment;

DETAILED DESCRIPTION

Figure 1A:
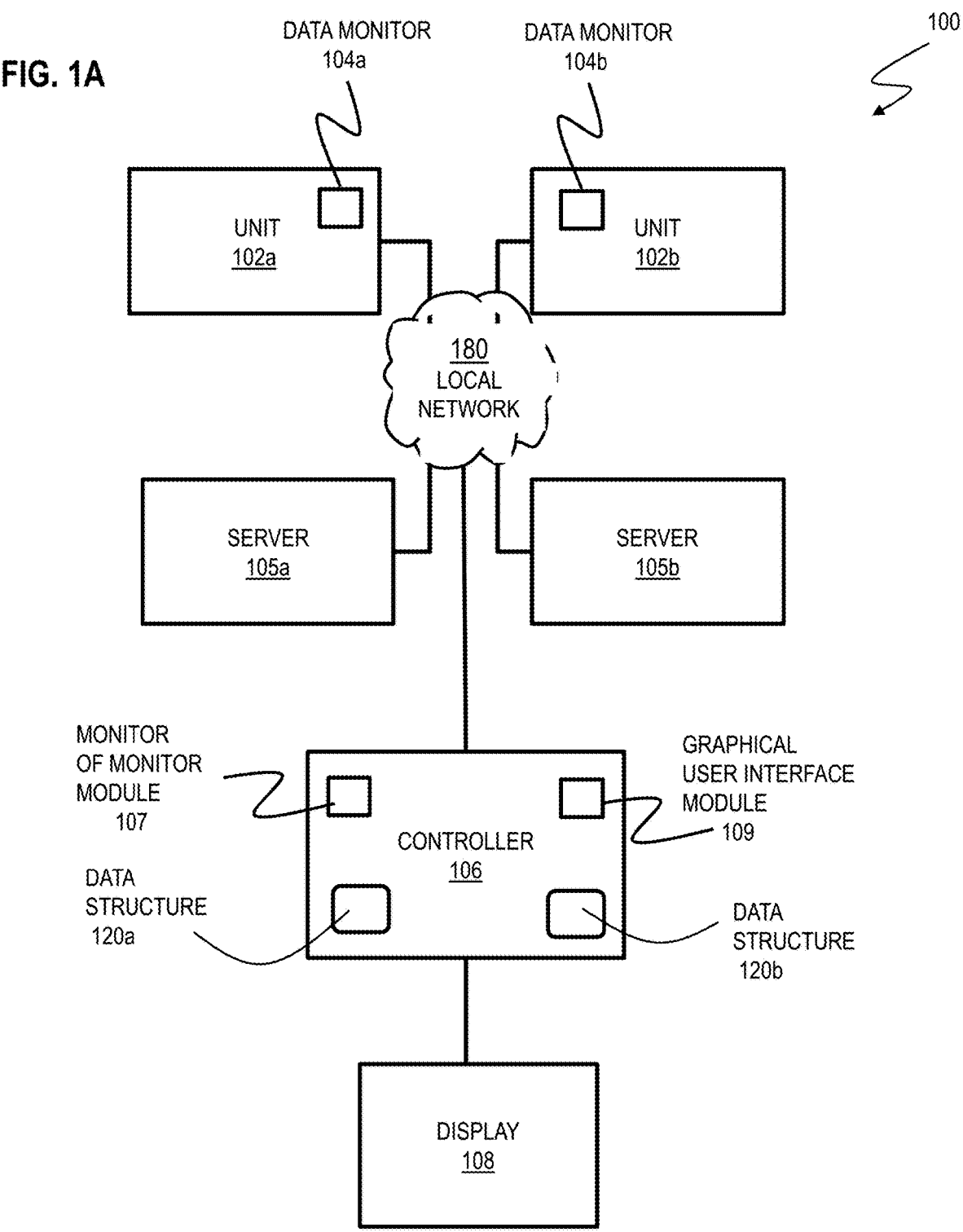
FIG. 1A is a block diagram that illustrates an example system for monitoring collection of physiological data, according to an embodiment.

A method and apparatus are described for monitoring collection of physiological data. Additionally, a method is described for presenting physiological data on a display. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus a value 1.1 implies a value from 1.05 to 1.15. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about X" implies a value in the range from 0.5X to 2X, for example, about 100 implies a value in a range from 50 to 200. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Some embodiments of the invention are described below in the context of the collection of physiological data from a plurality of physiological data monitors associated with a respective plurality of bed units in a medical facility, such as a hospital with one or more vital signs monitors available for each bed. Other embodiments of the invention are described below in the context of the display of the collected physiological patient data. However, the invention is not limited to these contexts. In various embodiments, the medical facility is a hospital, a mobile medical unit, such as a helicopter, plane, boat, train, or ambulance and the monitoring equipment includes devices for generating electrocardiograms (EKGs), electroencephalograms (EEGs) and other indicators on the state or condition of a patient. In some embodiments, the monitors provide other indicators of the state of other kinds of subjects, such as various equipment. For example, in various embodiments the subject condition data indicates the voltage at multiple power generators, or the central processor unit usage of various processors, or the rotation rate of various engines. As used herein the term "subject condition" refers to the conditions or state or function of a subject, including physiological data, like vital signs, for a patient of a medical facility. Furthermore, the term "unit" refers to a known location where a monitor is connected to a subject, such as a bed in a medical facility.

1. Overview for a Medical Facility

FIG. 1A is a block diagram that illustrates an example system 100 for monitoring collection of physiological data, according to an embodiment. The system 100 includes a plurality of subject condition data monitors 104a, 104b that are assigned to a respective plurality of units 102a, 102b in a facility, such as physiological monitors for bed units in a medical facility, as assumed for purposes of illustration in the following. In some embodiments, the system 100 excludes the bed units 102a, 101b. Although FIG. 1A depicts two bed units 102, in some embodiments the system 100 includes more than two bed units 102 that are divided into more than one group within the medical facility. For example, the groups include a trauma resuscitation unit (TRU), an operating room (OR) and a neural trauma critical care (NTCC), as further discussed below. In some embodiments, the medical facility is a hospital. In other embodiments, the medical facility is any location where healthcare is provided including clinics, doctor's offices, urgent care centers, residential treatment centers, or geriatric care facilities.

At each of a plurality of sample times, the physiological data monitors 104a, 104b measure a value of a parameter of physiological patient data and transmit the measured value and a value of the sample time to a plurality of servers 105a, 105b. In some embodiments, the physiological data monitors 104a, 104b, the servers 105a, 105b and a controller are connected through a local network 180. In some embodiments, the parameter of physiological patient data includes but is not limited to electrocardiographic (EKG), photoplethysmographic (PPG), carbon dioxide ($CO_2$), arterial blood pressure (ABP), intracranial pressure (ICP), heart rate (HR), respiratory rate (RR), temperature, oxygen saturation (SP02) and end-tidal $CO_2$ (EtCO2). Although FIG. 1A depicts two severs 105, in some embodiments the system 100 includes one server 105 or more than two servers 105. The controller 106 maintains a data structure for each server, such as data structure 120a for data reported by server 105a and data structure 120b for data reported by server 105b.

Figure 2:
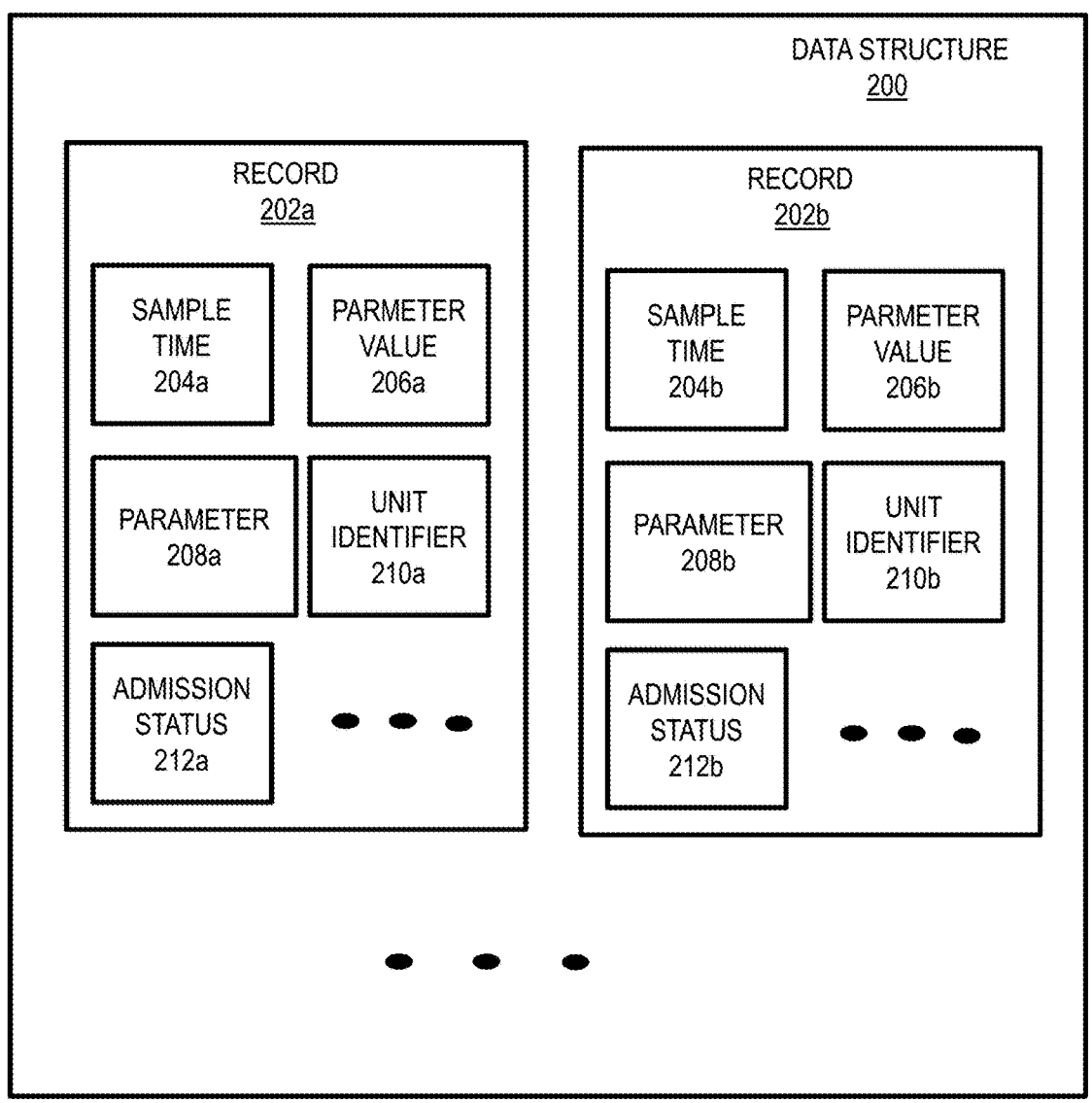
FIG. 2 is a block diagram that illustrates an example data structure used to store physiological patient data, according to an embodiment.

At each sample time, the measured value of the parameter of physiological patient data and the value of the sample time is transmitted from each server 105a, 105b to a controller 106. FIG. 2 is a block diagram that illustrates an example of a data structure 200 used to store physiological patient data, according to an embodiment. The data structure 200 resides as one of the data structures 120a or 120b, described above, on a computer-readable medium, such as a memory of the controller 106. In some embodiments, multiple data structures 200 are provided in the memory of the controller 106, where a respective data structure 200 is used to store physiological patient data from a respective server 105. The data structure 200 includes multiple records 202, where a respective record 202 is used to store the physiological patient data at a respective sample time. In an example embodiment, the physiological patient data at a first sample time is stored in a first record 202a and the physiological patient data at a second sample time is stored in a second record 201b.

Each record 202 includes multiple fields including a first field 204 for holding data indicating a value of the sample times for each bed unit 102 when a recorded value of the parameter of physiological patient data was received from the server for the physiological data monitor 104 associated with each bed unit 102. Each record 202 also includes a second field 206 for holding data indicating the value of the parameter of physiological patient data received from the server for the physiological data monitor 104 associated with each bed unit 102. In some embodiments, each record 202 also includes a third field 208 for holding data indicating the parameter of physiological patient data received from the server for physiological data monitor 104 associated with each bed unit 102.

Figure 1B:
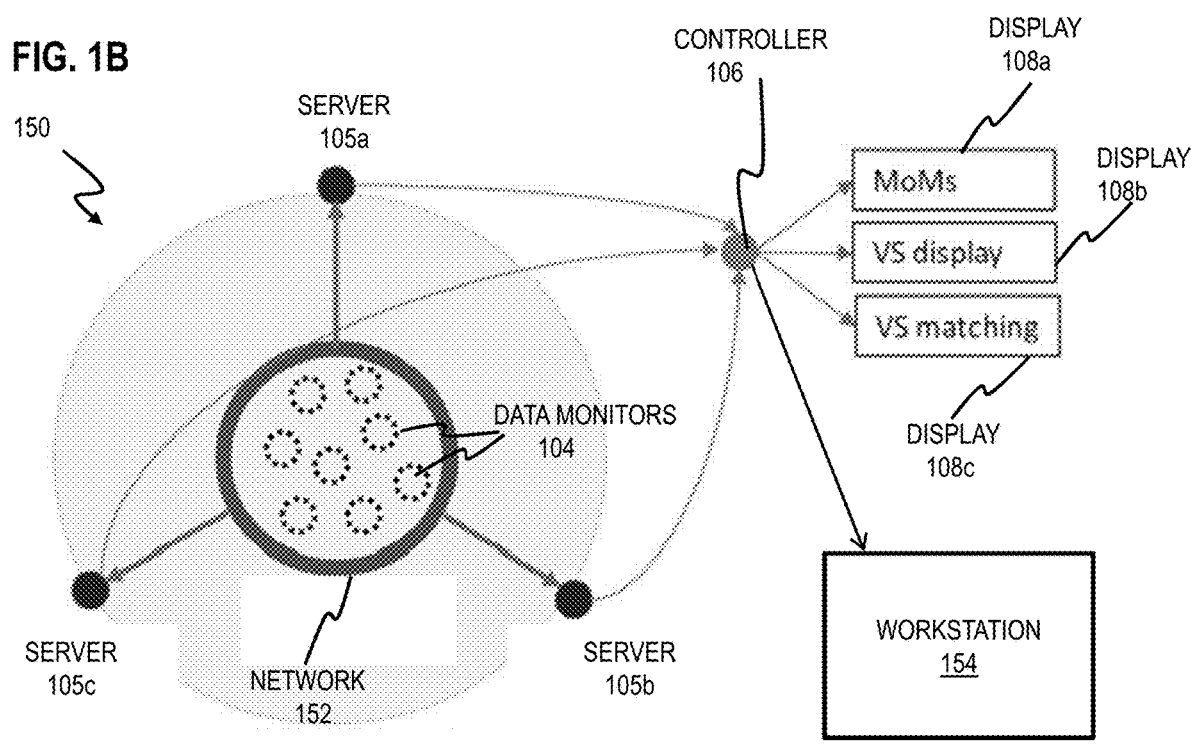
FIG. 1B is a block diagram that illustrates an example system for monitoring collection of physiological data, according to an embodiment.
Figure 1C:
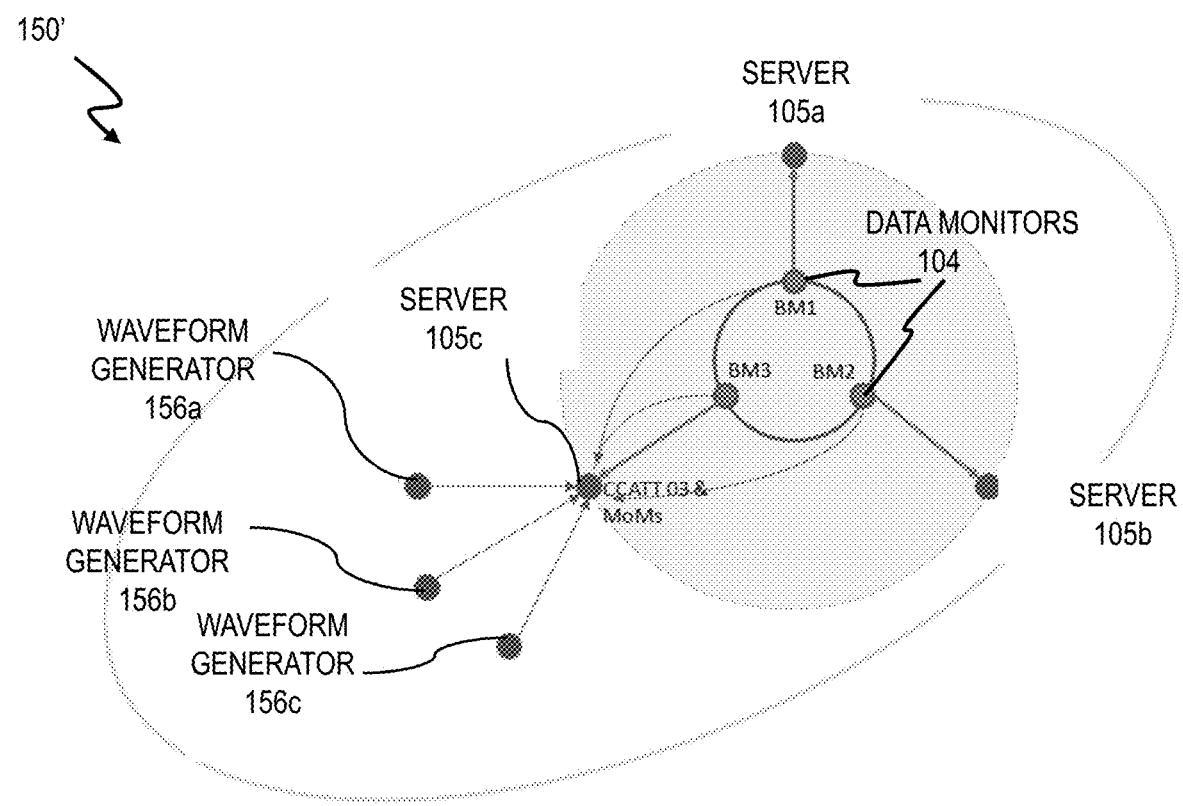
FIG. 1C is a block diagram that illustrates an example system for monitoring collection of physiological data, according to an embodiment.

Although processes, equipment, and data structures are depicted in FIG. 1A and FIG. 1B and FIG. 1C as integral blocks in a particular arrangement for purposes of illustration, in other embodiments one or more processes or data structures, or portions thereof, are arranged in a different manner, on the same or different hosts, in one or more databases, or are omitted, or one or more different processes or data structures are included on the same or different hosts.

Although data structures, messages and fields are depicted in FIG. 2, as integral blocks in a particular order for purposes of illustration, in other embodiments, one or more data structures or messages or fields, or portions thereof, are arranged in a different order, in the same or different number of data structures or databases in one or more hosts or messages, or are omitted, or one or more additional fields are included, or the data structures and messages are changed in some combination of ways.

In other embodiments, each bed unit 102 has a unique identifier. At each sample time, the physiological data monitor 104 associated with each bed unit 102 transmits the unique identifier to the server 105 which subsequently transmits the unique identifier to the controller 106. In this embodiment, each record 202 also includes a fourth field 210 for holding data indicating the identifier for each bed unit 102.

In other embodiments, each bed unit 102 has an admission status that indicates whether a patient is admitted (A) or discharged (D) from the bed unit 102. In some embodiments, the admission status is changed by medical staff (e.g. nurse) using a manual switch when the patient is admitted or discharged. At each sample time, the physiological data monitor 104 associated with each bed unit 102 transmits the admission status to the server 105 which subsequently transmits the admission status to the controller 106. In this embodiment, each record 202 also includes a fifth field 212 for holding data indicating the admission status for each bed unit 102.

Figure 8:
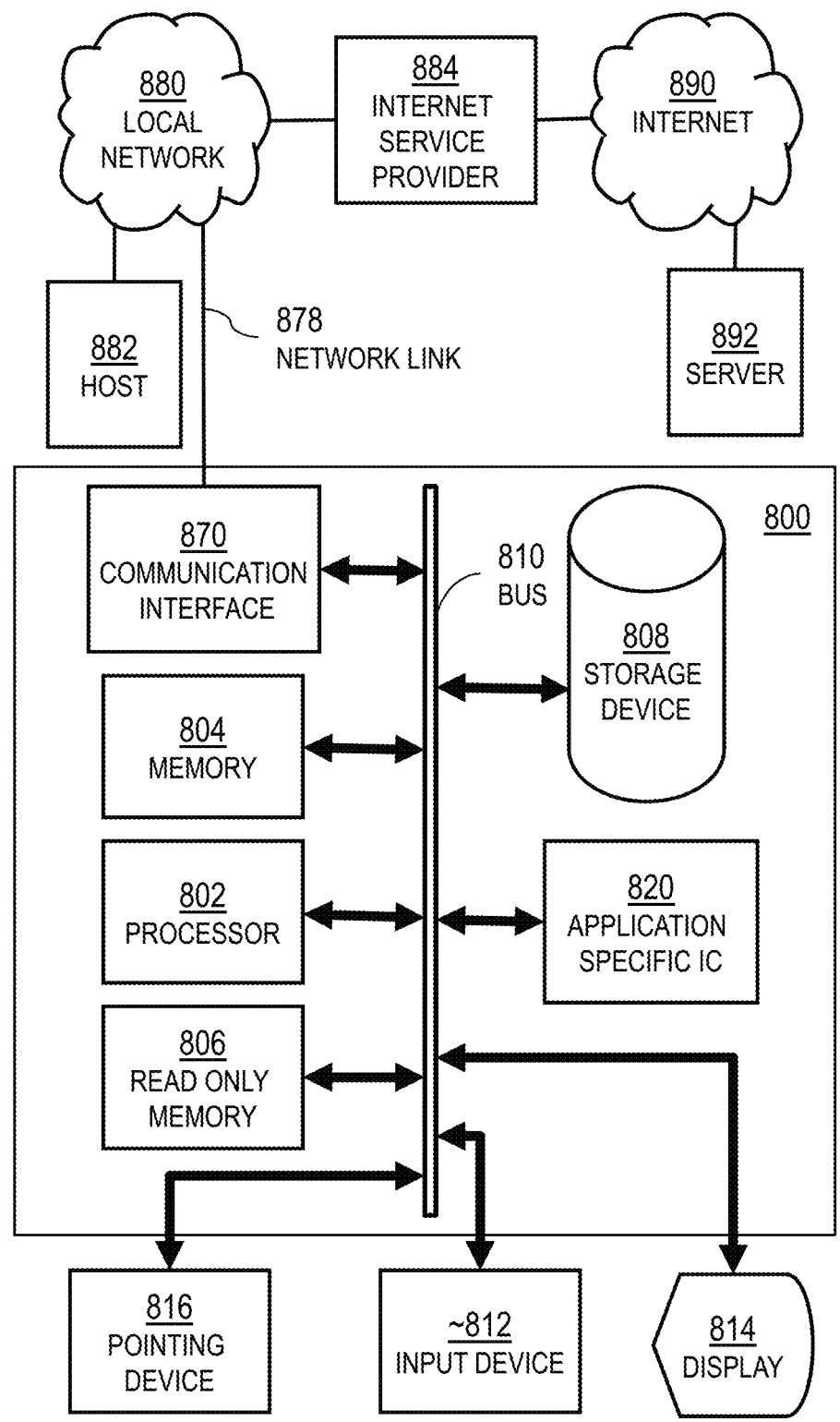
FIG. 8 is a block diagram that illustrates a computer system upon which an embodiment of the invention may be implemented.
Figure 9:
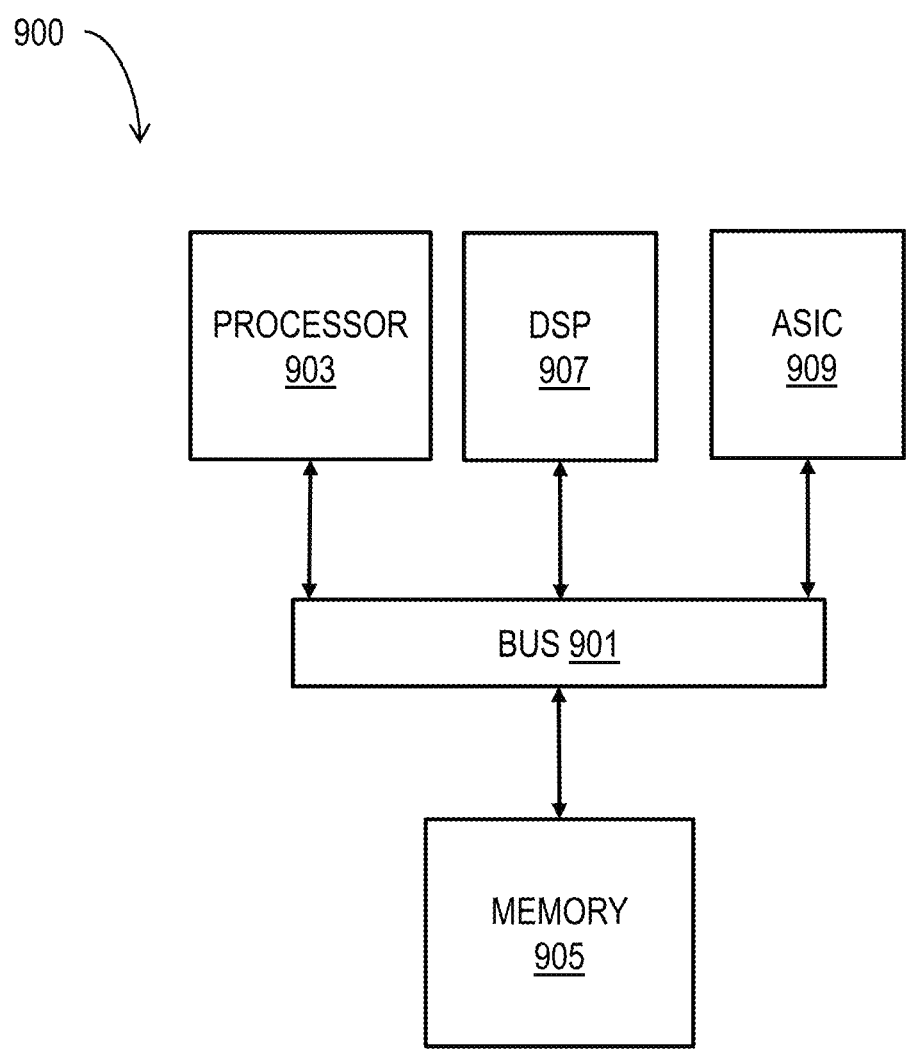
FIG. 9 is a block diagram that illustrates a chip set upon which an embodiment of the invention may be implemented.
Figure 10:
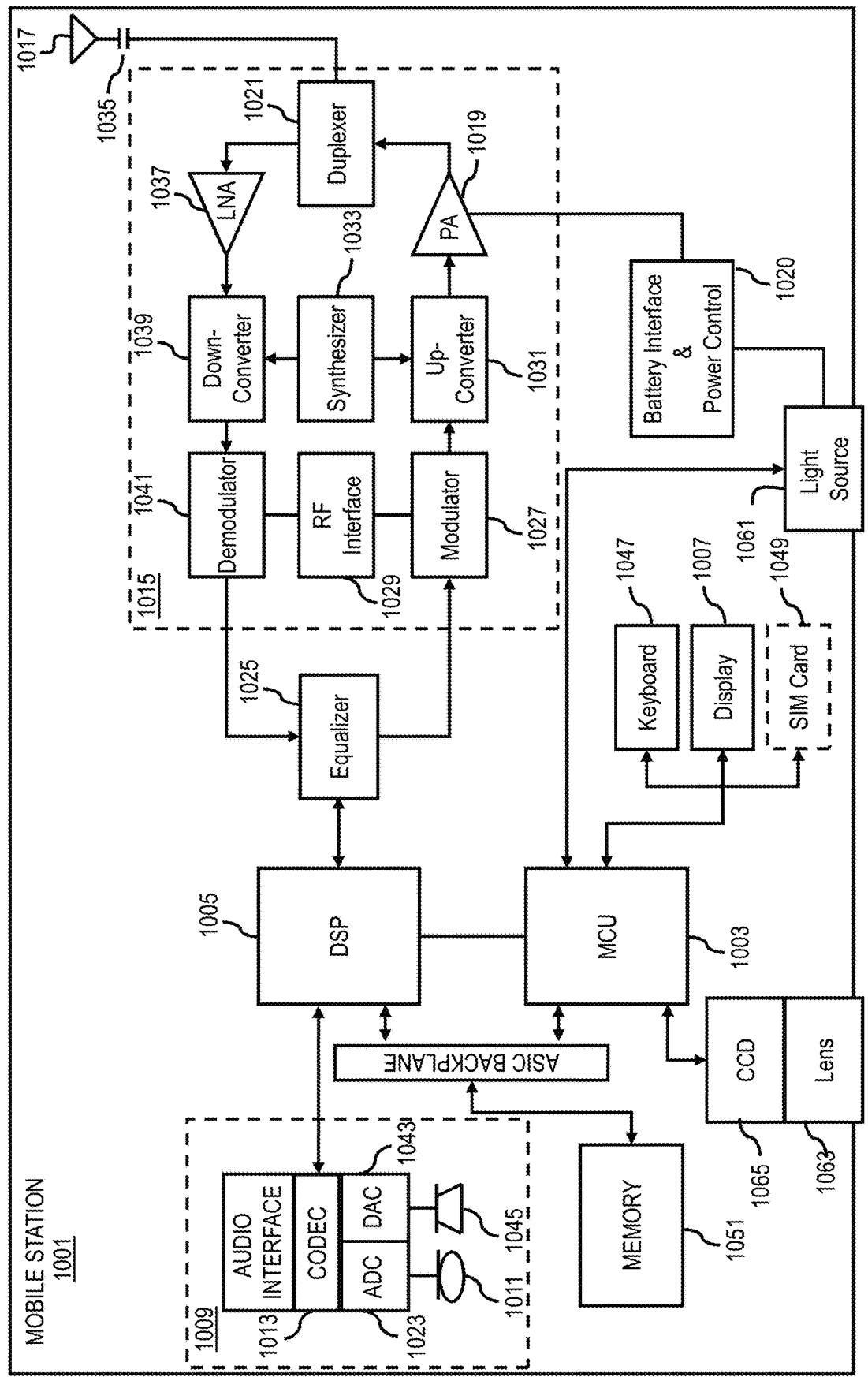
FIG. 10 is a block diagram that illustrates a mobile terminal upon which an embodiment of the invention may be implemented.

As illustrated in FIG. 1A, the controller 106 is configured to monitor the collection of physiological data and perform remedial action to diagnose and resolve detected gaps in the collection of physiological data and is connected to a display device 108, or other device, to present some or all the data in the one or more data structures, or otherwise remediate the situation detected. The controller 106 includes a monitor of monitor module 107 to perform one or more steps of a method described below with reference to FIG. 7A. In various embodiments, the controller 106 comprises one or more general purpose computer systems, as depicted in FIG. 8 or one or more chip sets as depicted in FIG. 9 or one or more mobile terminals as depicted in FIG. 10, and instructions to cause the computer or chip set or mobile terminal to perform one or more steps of a method described below with reference to FIG. 7A.

In some embodiments, for a current sample time, the module 107 determines a time gap defined by a duration between the current sample time and a most recent sample time. In one embodiment, the current sample time and the most recent sample time are retrieved from the first field 204 data of the data structure 202. In other embodiments, the time gap is stored in one of the fields (e.g. first field 204) of the data structure 202. In these embodiments, for the current sample time, the module 107 determines whether the time gap is greater than one or more time gap thresholds. The module 107 then causes the controller 106 to perform remedial action based on whether the time gap exceeds the one or more time gap thresholds. In some embodiments, the remedial action includes sending a communication to a person responsible for maintenance of the system, e.g., via email or text to a technician. In some embodiments, the remedial action involves transmitting a signal to the display 108 to present a plurality of indicators on the display 108 for each of the plurality of bed units 102. Each indicator provides a status of the collection of physiological data from the respective bed unit 102. In some embodiments, the indicator is color-coded based on whether the time gap for each bed unit 102 is greater than the one or more time gap thresholds. In some embodiments, the one or more time gap thresholds include a first time gap threshold (e.g. 5 minutes) and a second time gap threshold (e.g. 4 hours) that is greater than the first time gap threshold. In an embodiment, the color-coded indicator is a first colored indicator (e.g. green), if the time gap for the bed unit 102 is less than the first time gap threshold. In another embodiment, the color-coded indicator is a second colored indicator (e.g. yellow), if the time gap for the bed unit 102 is greater than the first time gap threshold but less than the second time gap threshold. In another embodiment, the color-coded indicator is a third colored indicator (e.g. red), if the time gap for the bed unit 102 is greater than the second time gap threshold. In one embodiment, a value of the first time gap threshold is small enough to achieve a relatively fast response (e.g. presenting the second colored indicator on the display 108) to an issue with the collection of physiological data. In another embodiment, the value of the first time gap threshold is large enough to avoid oversensitive response to insignificant network delays. In an example embodiment, the value of the first time gap threshold is in a range from about 2 minutes to about 10 minutes. In another example embodiment, the value of the second time gap threshold is in a range from about 1 hour to about 12 hours. In some embodiments, the values of the first time gap threshold and the second time gap threshold are adjustable.

Figure 3A:
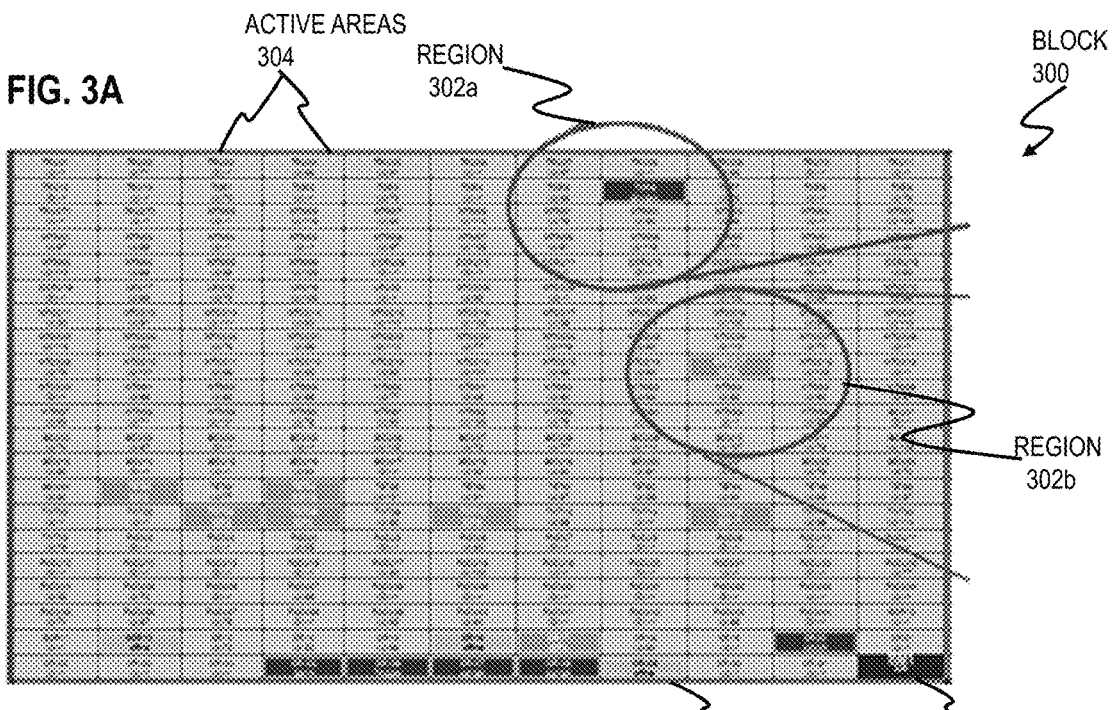
FIG. 3A is an image that illustrates an example of a block of active areas on the display of FIG. 1A, according to an embodiment.

FIG. 3A through FIG. 3C and FIG. 5A through FIG. 5E are diagrams of user interfaces utilized in the processes described herein, according to various embodiments. For example, FIG. 3A is an image that illustrates an example of a block 300 of active areas 304 on the display 108 of FIG. 1A, according to an embodiment. The screen includes one or more active areas 304 that allow a user to input data to operate on data. As is well known, an active area is a portion of a display to which a user can point using a pointing device (such as a cursor and cursor movement device, or a touch screen) to cause an action to be initiated by the device that includes the display. Well known forms of active areas are stand alone buttons, radio buttons, check lists, pull down menus, scrolling lists, and text boxes, among others. Although areas, active areas, windows and tool bars are depicted in FIG. 3A through FIG. 3C and FIG. 5A through FIG. 5E as integral blocks in a particular arrangement on particular screens for purposes of illustration, in other embodiments, one or more screens, windows or active areas, or portions thereof, are arranged in a different order, are of different types, or one or more are omitted, or additional areas are included or the user interfaces are changed in some combination of ways.

Figure 3B:
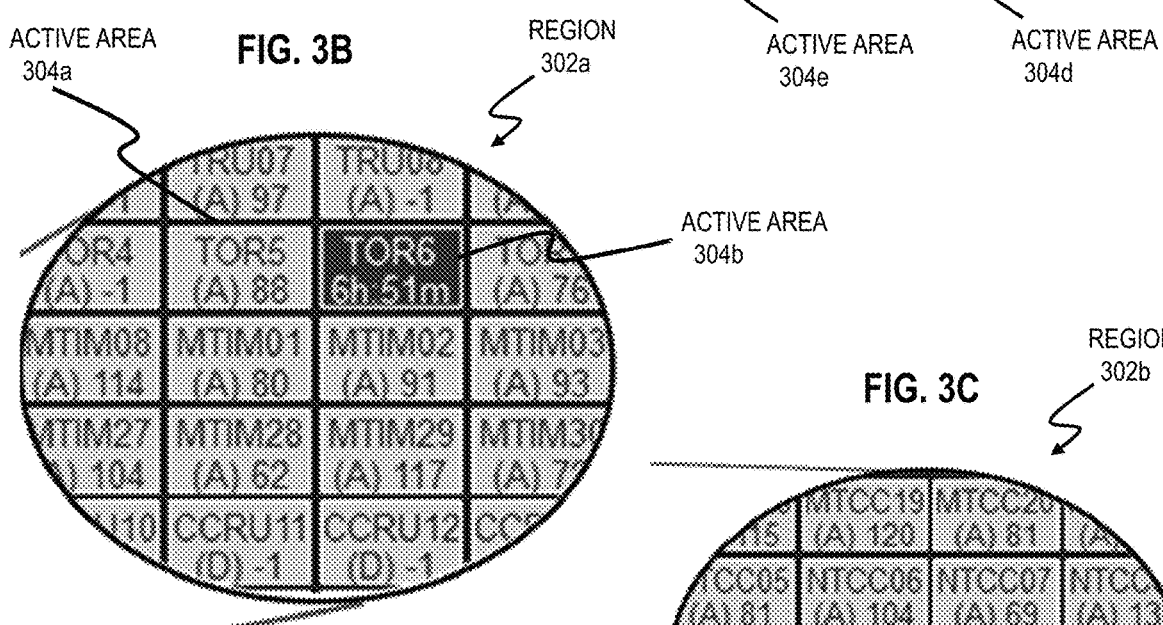
FIG. 3B is an image that illustrates an example of a region of the block of FIG. 3A, according to an embodiment.

As depicted in FIG. 3A, in some embodiments, each active area 304 presents a color-coded indicator associated with a respective bed unit 102. In some embodiments, the block 300 is specific to the physiological data provided by one server 105 and thus multiple blocks 300 can be generated based on the physiological data provided by the multiple servers 105. In one embodiment, the block 300 is a rectangular array of active areas 304. In another embodiment, the block 300 includes vertical columns or horizontal rows that are assigned to groups of bed units 102 within the medical facility. FIG. 3B is an image that illustrates an example of a region 302a of the block 300 of FIG. 3A, according to an embodiment. In an embodiment, a first active area 304a presents a green indicator and thus the bed unit 102 associated with the first active area 304a has a time gap at the current sample time that is less than the first time gap threshold. In an embodiment, a second active area 304b presents a red indicator and thus the bed unit 102 associated with the second active area 304b has a time gap at the current sample time that is greater than the second time gap threshold. In other embodiments, the indicators presented in the active areas 304 include the unique identifier of the bed unit 102 (e.g. TORS) indicated by the fourth field 210 data. In an example embodiment, the active areas 304 of the block 300 correspond to bed units 102 in a trauma resuscitation unit (TRU), an operating room (OR), a neurotrauma critical care unit (NTCC) and/or a multi-trauma critical care (MTCC) unit. In still other embodiments, the indicator presented in the active area 304a includes the value of the parameter of physiological patient data (e.g., 88) indicated by the second field 206 data. In still other embodiments, the indicator presented in the active area 304a includes the admission status (e.g., A) indicated by the fifth field 212 data. In still other embodiments, the indicator presented in the active area 304b includes the time gap (e.g., 6 h 51 m) calculated from the first field 204 data. In an example embodiment, the time gap is included in red and yellow indicators and the admission status and value of the parameter of physiological patient data are included in green indicators. In some embodiments, the block 300 only depicts active areas 304 where the time gap exceeds one of the first or second time gap thresholds (e.g. the block 300 only displays active areas 304 corresponding to bed units 102 with abnormal collection status based on yellow or red indicators). An advantage of this embodiment is that the block 300 can effectively monitor a greater number of bed units 102 since only those bed units 102 with abnormal collection statuses are displayed. In other embodiments, where the number of active areas 304 is less than a number of bed units 102 being monitored (e.g. the number of bed units 102 in a medical facility or a group within the medical facility), the display toggles between a first block 300 and a second block 300 (or more than two blocks 300) so that all of the bed units 102 are displayed over the two or more blocks 300 and where the toggle time between the blocks 300 is less than an incremental time when the physiological patient data is updated.

Figure 3C:
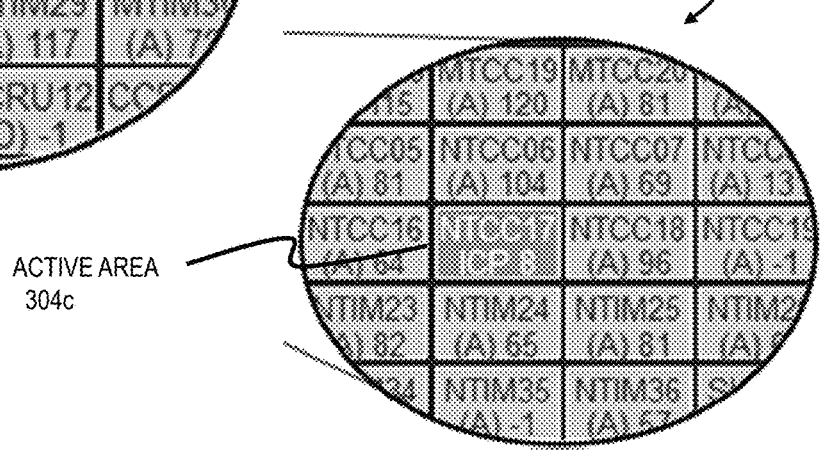
FIG. 3C is an image that illustrates an example of a different region of the block of FIG. 3A, according to an embodiment.

FIG. 3C is an image that illustrates an example of a region 302b of the block 300 of FIG. 3A, according to an embodiment. In this embodiment, an active area 304c within the region 302b presents a color-coded indicator based on the parameter of physiological patient data (e.g. intracranial pressure, ICP) indicated by the third field 208 data. In another embodiment, the color-coded indicator is based on the value of the parameter of physiological patient data (e.g., heart rate, HR>120) indicated by the second field 206 data. In some embodiments, the color-coded indicator is other than a green indicator, a yellow indicator or a red indicator (e.g. pink color indicator).

In some embodiments, the user can view the values of the parameter of physiological patient data associated with a particular bed unit 102. By an action of a pointing device the user selects a particular active area 304 associated with the particular bed unit 102. In one embodiment, the display 108 is a touchscreen and the user touches the particular active area 304. In response to this user action, the display 108 transmits a signal to the controller 106, wherein the signal identifies the particular bed unit 102. In some embodiments, a graphical user interface (GUI) module 109 of the controller 106 then transmits a signal to the display 108 including second field 206 data that indicate values of the parameter of physiological patient data from the particular bed unit 102. In an example embodiment, a trace plot 600 (FIG. 6A) is presented on the display 108 including the trace 608 of values of the parameter of physiological patient data from the particular bed unit 102. In another example embodiment, a unit view 550 (FIG. 5B) is presented on the display 108 of the particular bed unit 102.

FIG. 1B is a block diagram that illustrates an example system 150 for monitoring collection of physiological data, according to an embodiment. The system 150 of FIG. 1B is similar to the system 100 of FIG. 1A, with the exception that the system 150 includes three servers 105a, 105b, 105c and a network 152 of more than two physiological data monitors 104. In some embodiments, messages from the servers 105a, 105b, 105c to the controller 106, represented by curved lines in FIG. 1B, travel through the same or similar network as the local network 180 of FIG. 1A. Additionally, in some embodiments, the system 150 includes multiple screens that can be alternatively presented on a single display, or presented simultaneously on three different displays 108a, 108b, 108c, which screens are used to perform distinct functions of the system 150. In one embodiment, the display 108a is used to present a screen comprising the block 300 of active areas 304. In another embodiment, the display 108b is used to present a screen comprising an interactive graphical user interface (GUI) with displayed physiological data. In another embodiment, the display 108c is used present a screen configured to diagnose a gap in the collection of physiological data from one or more bed units 102. In an example embodiment, the display 108c screen is used to diagnose an instance when the time gap exceeds the one or more time gap thresholds. In some embodiments, the single display 108 is used and thus the features of each screen described above for display 108a, 108b, 108c are presented on the single display 108. Additionally, the system 150 includes a workstation 154 that can be located at the medical facility or remote from the medical facility. In one embodiment, the workstation 154 is a medical workstation configured for medical personnel (e.g. nurses) and is located at the medical facility. In another embodiment, the workstation 154 is configured for information technology (IT) personnel that are responsible for maintaining the connectivity of the system 150.

FIG. 1C is a block diagram that illustrates an example system 150' for monitoring collection of physiological data, according to an embodiment. The system 150' of FIG. 1C is similar to the system 150 of FIG. 1B with the exception that the system 150' includes three waveform generators 156a, 156b, 156c that generate a value of a waveform parameter of physiological patient data including but not limited to electrocardiographic (EKG) or photoplethysmographic (PPG). In some embodiments, the waveform generator 156a and data monitor 104a are associated with the same bed unit 104a, the waveform generator 156b and data monitor 104b are associated with the same bed unit 104b and the waveform generator 156c and data monitor 104c are associated with the same bed unit 104c. In these embodiments, the data monitors 104 measure a value of a parameter of physiological patient data other than the waveform parameter of physiological patient data. In an embodiment, the system 150' features a triple modular redundancy architecture which permits fast switch over time and high system availability. In one embodiment, one server 105c is selected as a principle or "backbone" server. If the selected backbone server 105c fails, values from a second server 105a or 105b will fill in. If the selected backbone server 105c and a second server 105a fail, values from the third server 105b fill in.

FIG. 4A is a graph that illustrates an example of a collection gap pattern 400a of physiological data at the plurality of servers 105a, 105b, 105c from the plurality of physiological data monitors 104 of FIG. 1B, according to an embodiment. Such a pattern can be presented on a screen for diagnosing gap patterns. The horizontal axis 402 represents time in arbitrary units. The vertical axis 404 represents distinct bed units 102 using the unique identifier. For each bed unit (e.g. TRU01, TRU02, etc), three data streams 406, 408, 410 represent recorded values of the parameter of physiological patient data received over time at the respective three servers 105a, 105b, 105c and reported to the controller 106. Grey bands indicate times when data is received from a server 105 but the physiological parameter value is absent, e.g., indicates a null value for the physiological parameter. This can occur when the monitor is in communication with the server 105, but the subject is not connected to the monitor, e.g., has been taken to a radiology laboratory. The three different shades of grey indicate the three different servers of FIG. 1B. A time gap 412 in the data stream 410a for a first bed unit 102 (e.g. TRU04) indicates that no records were received by the server 105c over the gap 412. In some embodiments, the time gap 412 exceeds one or more time gap thresholds. FIG. 4A depicts that the time gap 412 is present in the data stream 410 received at the third server 105c for every bed unit. In some embodiments, the module 107 automatically determines that the time gap 412, e.g., indicated by the first field 204 data for every bed unit 102 received from the server 105c exceeds the time gap threshold and consequently determines that the server 105c is offline. In this embodiment, the module 107 causes the controller 106 to perform a remedial action to resolve the time gap 412 and bring the server 105c back online. In one embodiment, the remedial action involves automatically transmitting an alert including an indication that the server 105c is offline. In an example embodiment, the alert is a communication message (e.g. email or text or both) to the workstation 154 that communicates to personnel at the workstation 154 that the server 105c is offline. In response to receiving the alert, personnel at the workstation 154 respond to the time gap 412, such as by rebooting the server 105c. In other embodiments, the remedial action involves automatically transmitting a signal to the server 105c to automatically reboot the server 105c. In other embodiments, a user observing the collection gap pattern 400a on the display 108 (or display 108c) visually determines that the server 105c is offline and subsequently transmits a communication message (e.g. email or text or both) to the workstation 154 to request that personnel at the workstation 154 bring the server 105c back online. In other embodiments, the communication message is an auditory alert message delivered to the workstation 154.

In some embodiments, the determination that the server 105c is offline gleaned from the collection gap pattern 400a of FIG. 4A can be similarly derived from the block 300 of FIG. 3A. In some embodiments, when the server 105c is offline, every active area 304 of the block 300 includes an indicator that the time gap exceeds the one or more time gap thresholds. In an example embodiment, when the server 105c is offline, every active area 304 of the block 300 includes a yellow indicator (e.g. if the time gap>5 minutes but<4 hours) or a red indicator (e.g. if the time gap is>4 hours).

FIG. 4A depicts non-null values 414 of the parameter of physiological patient data (e.g. HR) within each respective data stream 406, 408, 410. In some embodiments, non-null values 414 over a time period indicate a presence of a patient in the bed unit over that time period. Consequently, in some embodiments, the module 107 classifies a risk of loss of data collection for each time gap 412 based on whether the time gap 412 coincides with non-null values 414. In some embodiments, the time gap 412 in the data stream 410b from the TRU03 bed unit 102 (e.g. patient is present) may be classified as higher risk loss of data collection than the time gap 412 in the data stream 410a from TRU04 bed unit 102 (e.g. patient may not be present). This visual feature of the collection gap pattern 400a advantageously provides the user with information regarding potential data collection loss of each time gaps 412. For example, on unit TRU01, no patient is connected to a monitor until the last portion of the time period, while, in unit TRU02 and TRU03, each patient is intermittently connected to a monitor, as agreed by all functioning servers. Similarly, no patient is connected to a monitor at unit TRU04 during the entire time interval depicted.

Figure 4B:
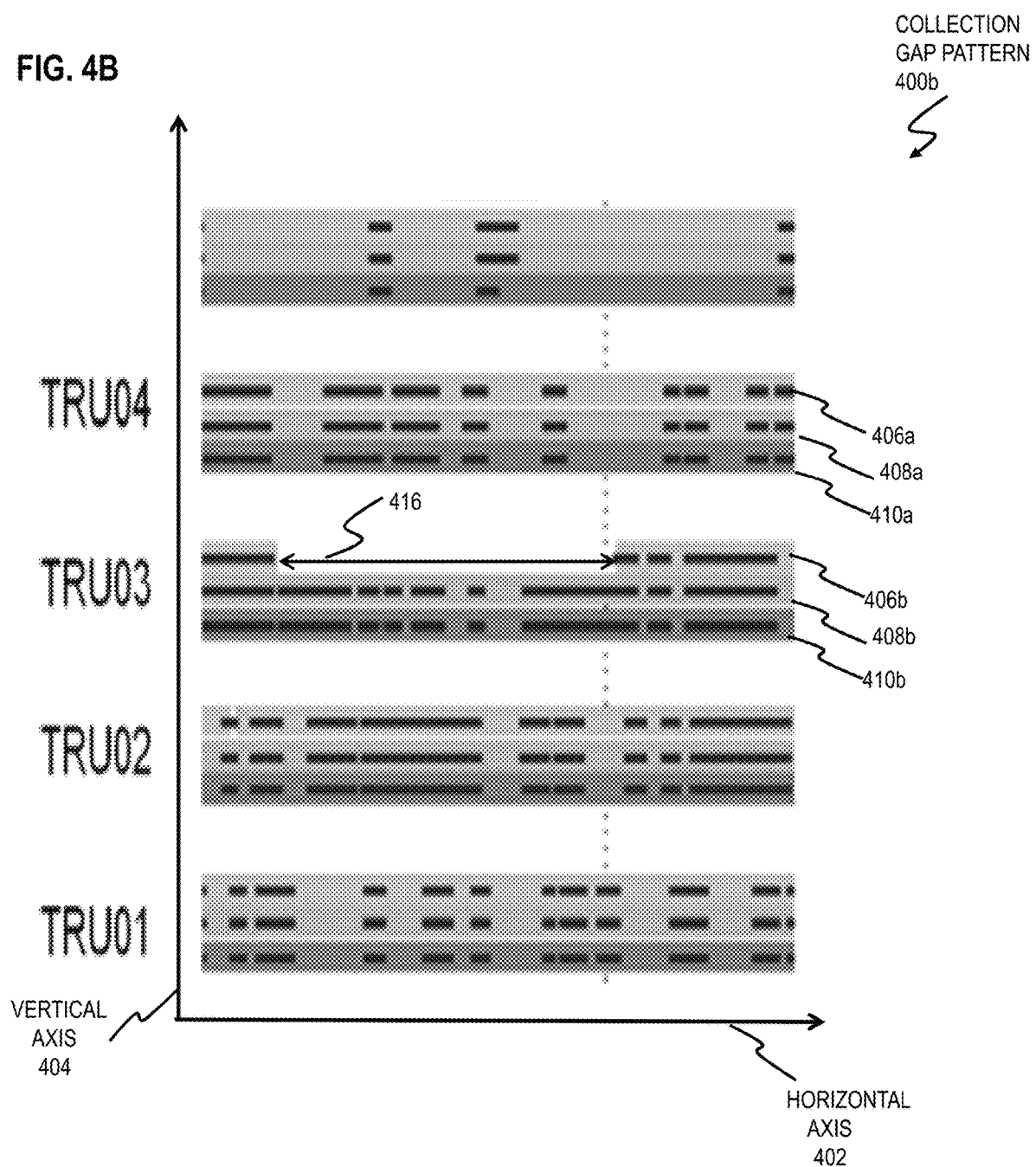
FIG. 4B is a graph that illustrates a second example collection gap pattern of physiological data at the plurality of servers from the plurality of physiological data monitors of FIG. 1B, according to an embodiment.

FIG. 4B is a graph that illustrates an example of a collection gap pattern 400b of physiological data at the plurality of servers 105a, 105b, 105c from the plurality of physiological data monitors 104 of FIG. 1B, according to an embodiment. In some embodiments, the module 107 stores physiological patient data (e.g. data stream 406) from the server 105a in a first data structure 200, stores physiological patient data (e.g. data stream 408) from the server 105b in a second data structure 200, and stores physiological patient data (e.g. data stream 410) from the server 105c in a third data structure 200. The horizontal axis 402 represents time in arbitrary units. The vertical axis 404 represents the distinct bed units 102 using the unique identifier. A time gap 416 in the data stream 406b from the server 105a associated with a first bed unit 102 (e.g. TRU03) indicates that no record was received by the server 105a over the time gap 416 from unit TRU03 only. In some embodiments, the time gap 416 exceeds the one or more time gap thresholds.

As depicted in FIG. 4B, no time gap is present in the data stream 406a from the server 105a associated with a second bed unit 102 (e.g. TRU04). Additionally, as depicted in FIG. 4B, no time gap is present in the data stream 408b from the server 105b associated with the first bed unit 102 (e.g. TRU03). Consequently, the time gap 416 is attributable to a disconnection between the first server 105a and the physiological data monitor 104 associated with the first bed unit 102 (e.g. TRU03).

In some embodiments, the module 107 automatically determines that the time gap 416, e.g. calculated from first field 204 data of the first data structure associated with the first bed unit 102 is greater than the at least one time gap threshold. Additionally, the module 107 automatically determines that time gaps calculated from the first field 204 data of the first data structure associated with the second bed unit 102 (e.g. data stream 406a) do not include a time gap exceeding the time gap threshold. Additionally, the module 107 automatically determines that time gaps calculated from the first field 204 data of the second data structure associated with the first bed unit 102 (e.g. data stream 408b) do not include a time gap exceeding the time gap threshold. Consequently, the module 107 automatically determines that there is a disconnection between the first server 105a and the physiological data monitor 104 associated with the first bed unit 102 (e.g. TRU03).

The module 107 then causes the controller 106 to perform a remedial action to respond to the time gap 416. In one embodiment, the remedial action involves automatically transmitting an alert including an indication that there is a disconnection between the first server 105a and the physiological data monitor 104 associated with the first bed unit 102. In an example embodiment, the alert is a communication message (e.g. email or text or both) to personnel at the workstation 154. In response to receiving the alert, personnel at the workstation 154 respond to the time gap 416, by reconnecting the first server 105a and the physiological data monitor 104 associated with the first bed unit 102. In other embodiments, a user observing the collection gap pattern 400b on the display 108 (or display 108c) visually determines that the time gap 416 is attributable to a disconnection between the first server 105a and the physiological data monitor 104 associated with the first bed unit 102 (e.g. TRU03). In this embodiment, the user subsequently transmits a communication message (e.g. email or text or both) to personnel at the workstation 154 to respond to the time gap 416 and reconnect the first server 105a and physiological data monitor 104.

FIG. 4B depicts non-null values 414 of the parameter of physiological patient data (e.g. HR) that can be used to classify the time gap 416 in a similar manner as in the collection gap pattern 400a.

In some embodiments, the determination of a disconnection between the first server 105a and the physiological data monitor 104 associated with the first bed unit 102 gleaned from the collection gap pattern 400b of FIG. 4B can be similarly derived from the block 300 of FIG. 3A. In some embodiments, this disconnection is recognized when the block 300 associated with the server 105a includes a first active area 304b (e.g. TRU03 bed unit) indicating that the time gap exceeds the time gap threshold and a second active area 304a (e.g. TRU04) that does not indicate that the time gap exceeds the time gap threshold. In an example embodiment, the disconnection is recognized when the first active area 304b includes a yellow indicator or red indicator and the second active area 304a includes a green indicator.

FIG. 4C is a graph that illustrates an example of a collection gap pattern 400c of physiological data at the plurality of servers 105a, 105b, 105c from the plurality of physiological data monitors 104 of FIG. 1B, according to an embodiment. The horizontal axis 402 represents time in arbitrary units. The vertical axis 404 represents the distinct bed units 102 using the unique identifier. A time gap 418 in the data streams 406c, 408c, 410c from the respective servers 105a, 105b, 105c associated with a first bed unit 102 (e.g. TRU02) indicates that no records were received from the first bed unit 102 over the time gap 418. In some embodiments, the time gap 418 exceeds the one or more time gap thresholds. As depicted in FIG. 4C, the time gap 418 is present in the data streams 406c, 408c, 410c of each server 105a, 105b, 105c associated with the first bed unit 102 (e.g. TRU02) and no time gap is present in the data streams 406b, 408b, 410b of each server 105a, 105b, 105c associated with a second bed unit 102 (e.g. TRU03). Consequently, the time gap 418 is attributable to a disconnection between every server 105a, 105b, 105c and the physiological data monitor 104 associated with the first bed unit 102 (e.g. TRU02).

In some embodiments, the module 107 automatically determines that the time gap 418, i.e. calculated from first field 204 data of the first data structure, second data structure and third data structure associated with the first bed unit 102 (e.g. TRU02) is greater than the at least one time gap threshold. Additionally, the module 107 automatically determines that time gaps calculated from the first field 204 data of the first data structure, second data structure and third data structure associated with the second bed unit 102 (e.g. TRU03) do not include a time gap exceeding the time gap threshold. Consequently, the module 107 automatically determines that there is a disconnection between every server 105a, 105b, 105c and the physiological data monitor 104 associated with the first bed unit 102 (e.g. TRU02). The module 107 then causes the controller 106 to perform a remedial action to resolve the time gap 418.

In one embodiment, the remedial action involves automatically transmitting an alert including an indication that there is a disconnection between each server 105a, 105b, 105c and the physiological data monitor 104 associated with the first bed unit 102. In an example embodiment, the alert is a communication message (e.g. email or text or both) to personnel at the workstation 154. In response to receiving the alert, the personnel respond to the time gap 418, by reconnecting the servers 105a, 105b, 105c and the physiological data monitor 104 associated with the first bed unit 102. In other embodiments, a user observing the collection gap pattern 400c on the display 108 (or display 108c) visually determines that the time gap 418 is attributable to a disconnection between every server 105a, 105b, 105c and the physiological data monitor 104 associated with the first bed unit 102 (e.g. TRU02). In this embodiment, the user subsequently transmits a communication message (e.g. email or text or both) to personnel at the workstation 154 to respond to the time gap 418 and reconnect each server 105a, 105b, 105c and physiological data monitor 104. FIG. 4C depicts non-zero values 414 of the parameter of physiological patient data (e.g. HR) that can be used to classify the time gap 418 in a similar manner as in the collection gap pattern 400a.

In some embodiments, the determination of a disconnection between every server 105a, 105b, 105c and the physiological data monitor 104 associated with the first bed unit 102 gleaned from the collection gap pattern 400c of FIG. 4C can be similarly derived from the block 300 of FIG. 3A. In some embodiments, this disconnection is recognized when the multiple blocks 300 associated with each of the servers 105a, 105b, 105c includes a first common active area 304b (e.g. TRU02 bed unit) indicating that the time gap exceeds the time gap threshold and a second common active area 304a (e.g. TRU03) that does not indicate that the time gap exceeds the time gap threshold. In an example embodiment, the first common active area 304b includes a yellow indicator or red indicator and the second common active area 304a includes a green indicator.

In an example embodiment, Table 1 below depicts a diagnosis for various collection gap patterns, including the collection gap patterns of FIGS. 4A-4C.

TABLE 1

|  | Failure type | MoMs indicator |
| --- | --- | --- |
| BedMaster software | 1. Individual bed unit configuration error | Random cells in yellow/red |
|  | 2. BedMaster database error | A block of cells in yellow/red; BedMaster server is online |
|  | 3. BedMaster service down | A block of cells in yellow/red; BedMaster service stopped |
| BedMaster hardware | 1. BedMaster server down | A block of cells in yellow/red; BedMaster server is offline |
| Network | 1. BedMaster server connection failure | Random cells in yellow/red |

In another example embodiment, the monitor of monitor module 107 features software in a high level programming language (e.g. Matlab® R2014a, Mathworks, Boston Mass.) that preprocesses the physiological parameter data so that it is aligned in the time domain in the collection gap patterns depicted in FIGS. 4A-4C.

Figure 7A:
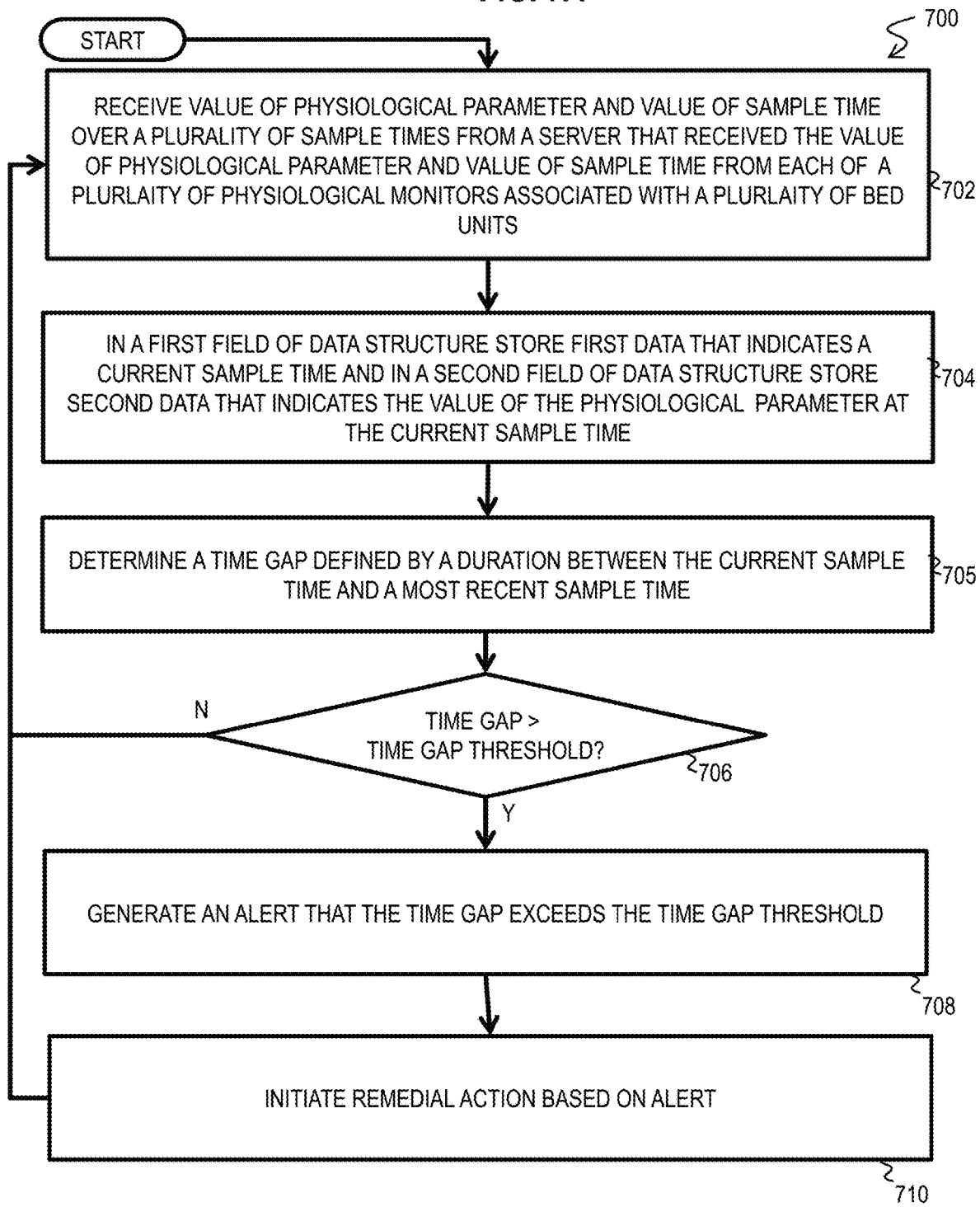
FIG. 7A is a flow diagram that illustrates an example of a method for monitoring collection of physiological data, according to an embodiment.
Figure 7B:
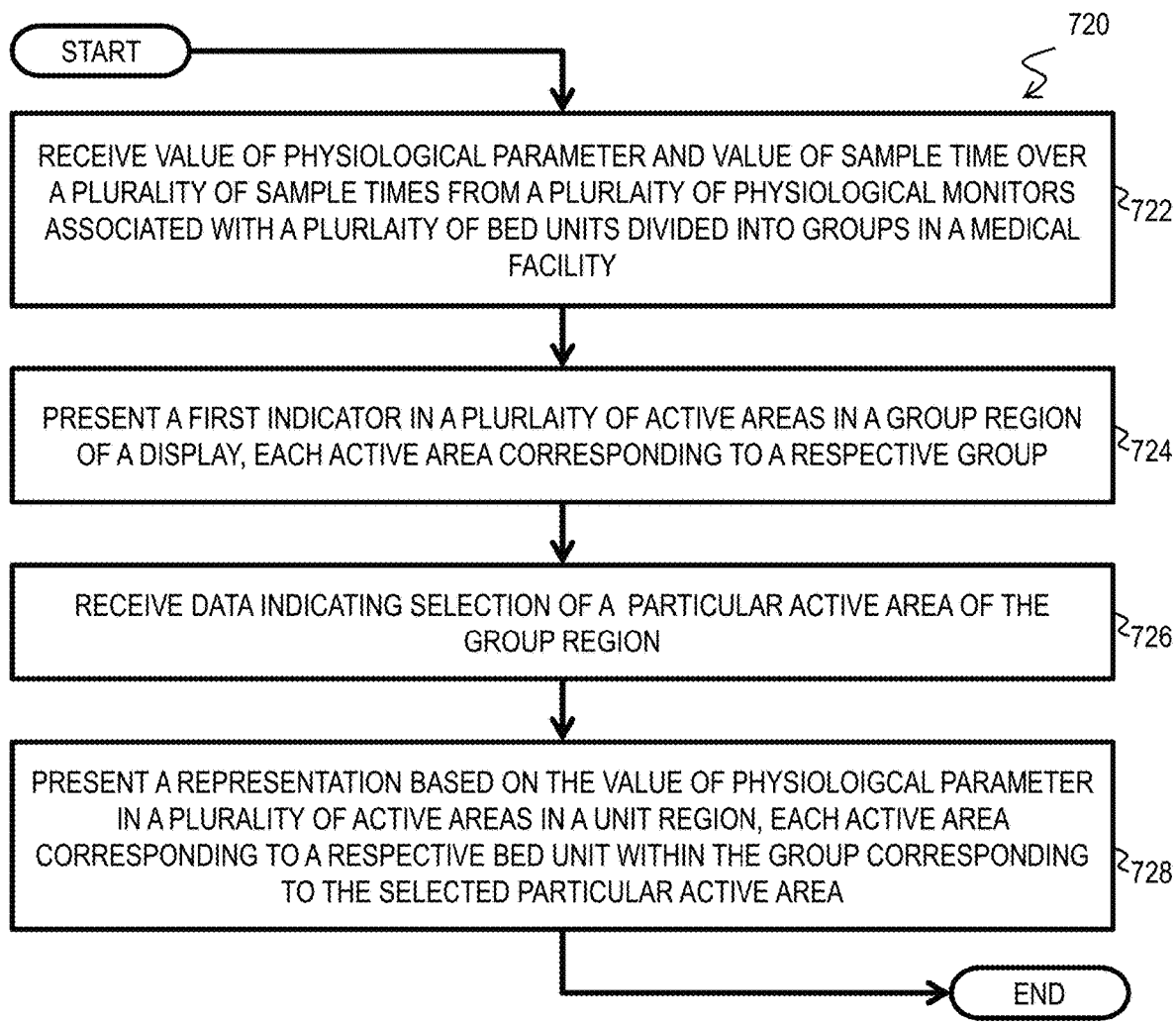
FIG. 7B is a flow diagram that illustrates an example of a method for displaying a group view of physiological data collected from a plurality of bed units divided into groups in a medical facility, according to an embodiment.

Although steps are depicted in FIGS. 7A-7C, as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

FIG. 7A is a flow diagram that illustrates an example of a method 700 for monitoring collection of physiological data, according to an embodiment. In step 702, the value of the parameter of physiological patient data and the value of the sample time is received at the controller 106 from each server 105a, 105b. In one embodiment, step 702 is performed at each sample time. In an example embodiment, the sample times occur every 1 minute. In some embodiments, two servers 105a, 105b (FIG. 1A) are employed during step 702. In other embodiments, one server 105 or more than two servers (e.g. FIG. 1B) are employed during step 702. In some embodiments, at each sample time, the servers 105a, 105b each receive the value of the parameter of physiological patient data and the value of the sample time from each of the plurality of physiological data monitors 104 associated with the plurality of bed units 102.

In step 704, data is stored in the first field 204 of the data structure 200 that indicates the value of the sample time when the value of the parameter of physiological patient data is received in step 702. In some embodiments, step 704 is performed at a current sample time and the value of the current sample time is stored in the first field 204. Additionally, in step 704, data is stored in the second field 206 that indicates the value of the parameter of physiological patient data received in step 702. Where values for more than one parameter of physiological patient data is received in step 702, second field 206 data is stored that indicates these values in step 704. In some embodiments, step 704 is performed at the current sample time and the value of the parameter of physiological patient data received at the current sample time is stored in the second field 206. If no value is reported by the monitor for a particular physiological parameter, a null value is stored in the field. The field is recorded to indicate that a record was received from the server.

In step 705 a time gap is defined as the duration between the current sample time and a most recent sample time when a recorded value of the parameter of physiological patient data was received at step 702. In some embodiments, in step 705, the current sample time and the most recent sample time are retrieved from the first field 204. In other embodiments, in step 704 the time gap is stored in one of the fields (e.g. first field 204) of the data structure 200 and step 705 is omitted.

In step 706, a determination is made at the current sample time regarding the time gap determined in step 705. In one embodiment, in step 706, a determination is made whether the time gap calculated by the first field 204 data exceeds one or more time gap thresholds stored in a memory of the controller 106. In an example embodiment depicted in FIG. 3A, the time gap threshold is the first time gap threshold (e.g. 5 minutes). In another example embodiment, the time gap threshold is the second time gap threshold (e.g. 4 hours) that is longer than the first time gap threshold. In some embodiments, in step 706, the determination further includes a determination of a cause of the time gap exceeding the one or more time gap thresholds. In an example embodiment, in step 706, the determination is made whether the time gap exceeding the time gap threshold is attributable to one of the servers 105 being offline (FIG. 4A). In another example embodiment, in step 706, the determination is made whether the time gap exceeding the time gap threshold is attributable to a disconnection between one of the servers 105 and the physiological data monitor 104 associated with one of the bed units 102 (FIG. 4B). In another example embodiment, in step 706, the determination is made whether the time gap exceeding the time gap threshold is attributable to a disconnection between every server 105 and the physiological data monitor 104 associated with one of the bed units 102 (FIG. 4C). If the determination in step 706 is negative, then the method 700 proceeds back to step 702. If the determination in step 706 is positive, then the method 700 proceeds to step 708.

In step 708, an alert is generated that the time gap exceeds one or more time gap thresholds. In one embodiment, the alert is generated by presenting the block 300 of active areas 304 on the display 108, where the color-coded indicator within each active area 304 is based on the determination of step 706. In other embodiments, the alert is generating by transmitting a communication message (e.g. email or text or both) to personnel at the workstation 154 to respond to the time gap. In an example embodiment, the communication message identifies the one or more bed units 102 where the time gap exceeds the time gap threshold. In another example embodiment, where the determination in step 706 includes a determination of the cause of the time gap exceeding the time gap threshold, the communication message identifies the determined cause (e.g. server 105 is offline, physiological data monitor 104 is disconnected from server 105, etc.).

In step 710, remedial action is initiated based on the generated alert of step 708. In one embodiment, the remedial action includes responding to the time gap that exceeds the one or more time gap thresholds. In one embodiment, where the communication message from step 708 identifies one or more bed units 102 where the time gap exceeds the time gap threshold, the remedial action involves checking the status of the physiological data monitors 104 associated with the one or more bed units 102 to ensure the physiological data monitors 104 are functional. In other embodiments, the remedial action involves checking that the one or more servers 105 are online and rebooting any servers 105 that are identified as offline. In one embodiment, where the communication message from step 708 identifies that the cause of the time gap exceeding the time gap threshold is that one or more servers 105 is offline, the remedial action involves verifying that the one or more servers 105 are offline and rebooting the one or more servers 105. In yet another embodiment, where the communication message from step 708 identifies that the cause of the time gap exceeding the time gap threshold is a disconnection between one or more servers 105 and a physiological data monitor 104 of one of the bed units 102, the remedial action involves checking the connection between the one or more servers 105 and the physiological data monitor 104 and reconnecting the one or more servers 105 with the physiological data monitor 104. After performing the remedial action in step 710, the method 700 proceeds back to step 702. In step 706, the determination of whether the time gap exceeds the time gap threshold is repeated, in order to verify whether the remedial action in step 710 was effective in eliminating the time gap.

As illustrated in FIG. 1A, the controller 106 is connected to the display 108, to present the physiological patient data. In some embodiments, the display 108 is the same as the display 108 used to present the indicators for each bed unit 102 (e.g. the block 300 of active areas 304) for monitoring collection of the physiological patient data. In other embodiments, the controller generates a separate screen that is presented on the same or a separate display, e.g., display 108b (FIG. 1B) to present the physiological patient data, where the separate screen is configured for viewing by medical professionals to determine the state or care, or both, of a patient in one or more of the bed units. In some embodiments, it is advantageous for the screen to be presented on the display 108b that is separate from the display 108a used to present the indicators for each bed unit 102 to monitor the collection of physiological patient data.

In some embodiments, the controller 106 receives the value of the parameter of physiological patient data and the value of the sample time from the servers 105a, 105b. In other embodiments, the servers 105a, 105b are omitted and the controller 106 receives the value of the parameter of physiological patient data and the value of the sample time from the physiological data monitors 104. The controller 106 includes a graphical user interface (GUI) module 109 to perform one or more steps of a method described below with reference to FIG. 7B or a method described below with reference to FIG. 7C. In various embodiments, the controller 106 comprises one or more general purpose computer systems, as depicted in FIG. 8 or one or more chip sets as depicted in FIG. 9, and instructions to cause the computer or chip set to perform one or more steps of a method described below with reference to FIG. 7B or FIG. 7C. In some embodiments a screen is generated for presentation on a display to present physiological patient data related to monitoring a plurality of patients in a respective plurality of bed units 102 of a medical facility. In some embodiments, the plurality of bed units 102 are divided into one or more groups or clinical divisions of the medical facility. In one embodiment, the groups include a trauma resuscitation unit (TRU), an operating room (OR), and a neural trauma critical care (NTCC).

Figure 5A:
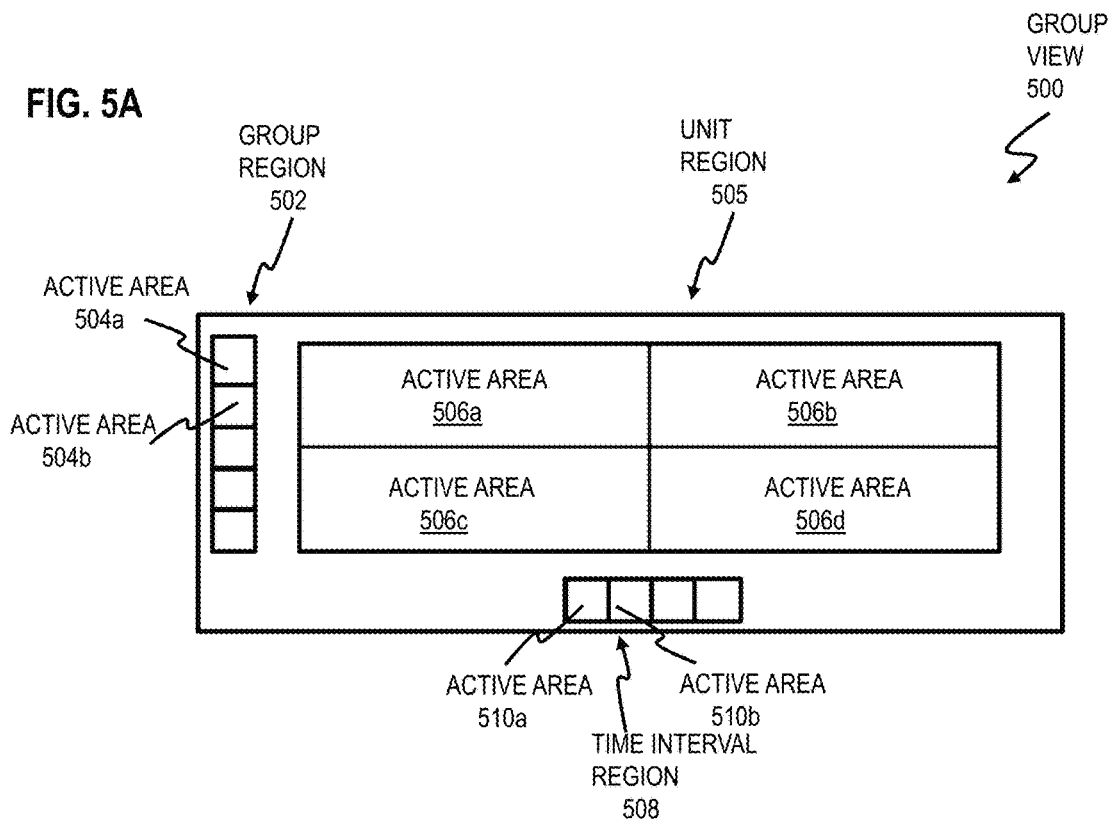
FIG. 5A is a block diagram that illustrates an example of a group view for displaying physiological patient data, according to an embodiment.

FIG. 5A is a block diagram that illustrates an example of a group view 500 for displaying physiological data of patients in a single group of the medical facility, according to an embodiment. In one embodiment, the group view 500 is a screen that includes an indicator in a plurality of active areas 504a, 504b in a group region 502. In some embodiments, each active area 504 corresponds to a respective group in the medical facility. In some embodiments, the indicator in each active area 504 is an acronym of the name of the group (e.g. TRU for trauma resuscitation unit). In other embodiments the indicator is a thumbnail image or icon representing the group. In other embodiments, multiple active areas 504 correspond to a respective group in the medical facility. Although FIG. 5A depicts five active areas 504, the group region 502 is not limited to five active areas 504 and can include more or less active areas 504 in order to match the number of groups in the medical facility.

The group view 500 further includes a plurality of active areas 506a, 506b, 506c, 506d in a unit region 505, where each active area 506 corresponds to a respective bed unit 102 in a particular group associated with a particular active area 504a in the group region 502. In one embodiment, in response to a selection by a single or other action of a pointing device within the particular active area 504a, the value of the parameter of physiological patient data for each bed unit 102 in the particular group is displayed in a respective active area 506. In some embodiments, in response to the selection of the particular active area 504a, a representation of the value of the parameter of physiological patient data is presented in the respective active area 506. In one embodiment, the representation is a trace 608 (FIG. 6A) of the value of the parameter of physiological patient data along a time axis. In another embodiment, the representation is a bar 656 (FIG. 6B) that indicates an occurrence of the value of the parameter of physiological patient data along a time axis. In an example embodiment, a first color (e.g. green) of the trace or bar indicates that the value of the parameter is below a first threshold value and a second color (e.g. yellow, red) of the trace or bar indicates that the value of the parameter is above a second threshold value. In one example embodiment, the first threshold value is the same as the second threshold value. In another example embodiment, the first threshold value is not the same as the second threshold value and a third color (e.g. yellow) of the trace or bar indicates that the value of the parameter is above the first threshold value and below the second threshold value. In an example embodiment, the display 108 is a touchscreen and the single action of selecting the particular active area 504a is touching the particular active area 504a.

In some embodiments, the unit region 505 includes a fixed number of active areas 506. In these embodiments, where the number of bed units 102 in the single group exceeds the fixed number of active areas 506, multiple active areas 504 in the group region 502 are used to designate a single group. In an example embodiment, the indicator in the multiple areas 504 include an acronym for the group and an alpha or numeric character or other indicator, such as color or hatching, to represent a subgroup within the single group (e.g. TRU-A and TRU-B). Although FIG. 5A depicts that the unit region 505 includes a specific fixed number (e.g., four) active areas 506, the unit region 505 is not limited to this fixed number of active areas and can feature less or more fixed number of active areas 506. Additionally, in other embodiments, the unit region 505 includes an automatically or manually adjustable number of active areas 506, where a size of each active area 506 changes based on the number of active areas 506 (e.g., larger active area 506 for a smaller number of active areas 506 and a smaller active area 506 for a larger number of active areas 506).

Figure 5B:
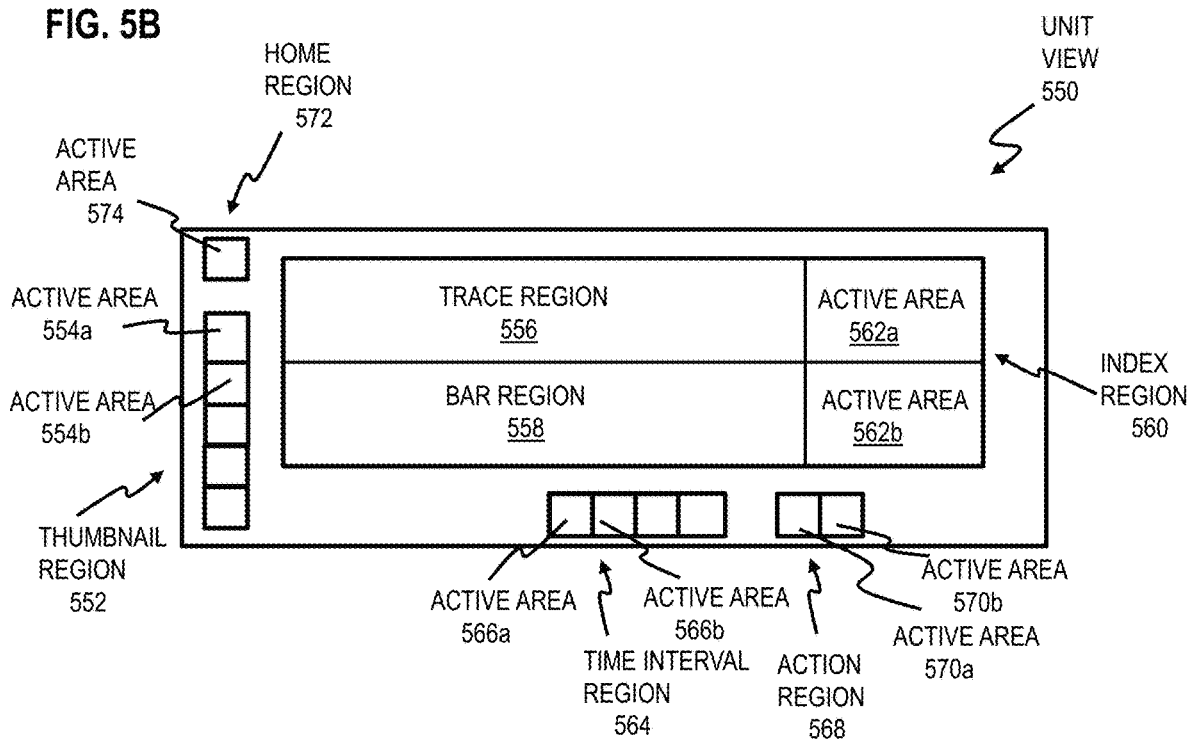
FIG. 5B is a block diagram that illustrates an example of a unit view for displaying physiological patient data, according to an embodiment.
Figure 5C:
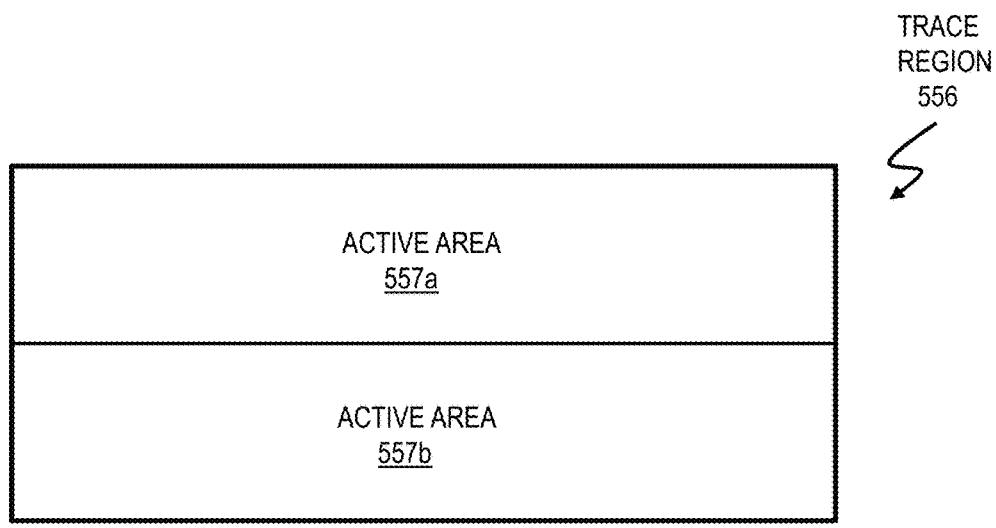
FIG. 5C is a block diagram that illustrates an example of a trace region of the unit view of FIG. 5B, according to an embodiment.
Figure 5D:
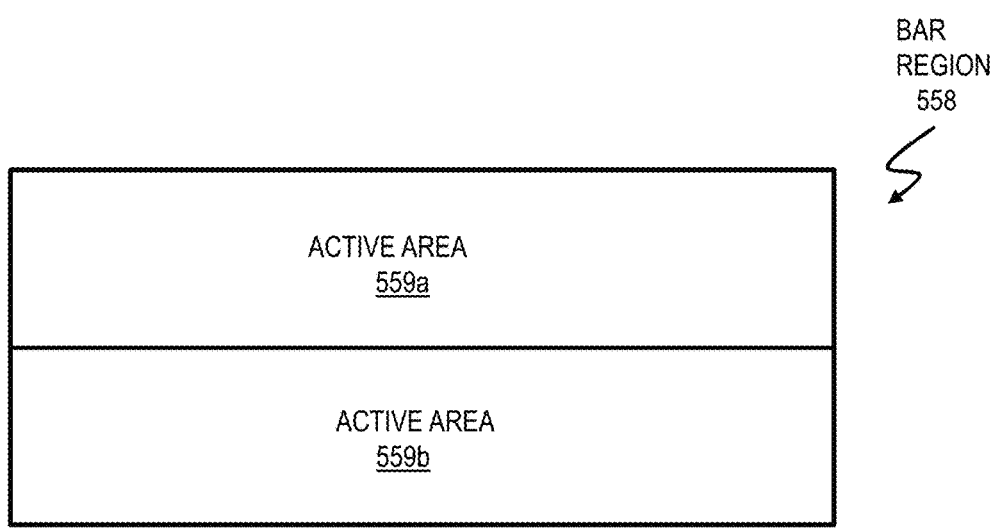
FIG. 5D is a block diagram that illustrates an example of a bar region of the unit view of FIG. 5B, according to an embodiment.
Figure 5E:
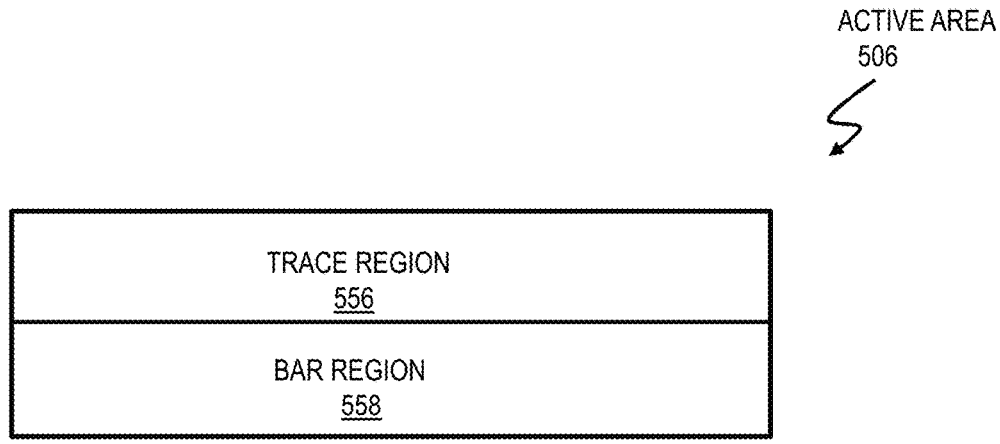
FIG. 5E is a block diagram that illustrates an example of an active area of the group view of FIG. 5A, according to an embodiment.
Figure 6A:
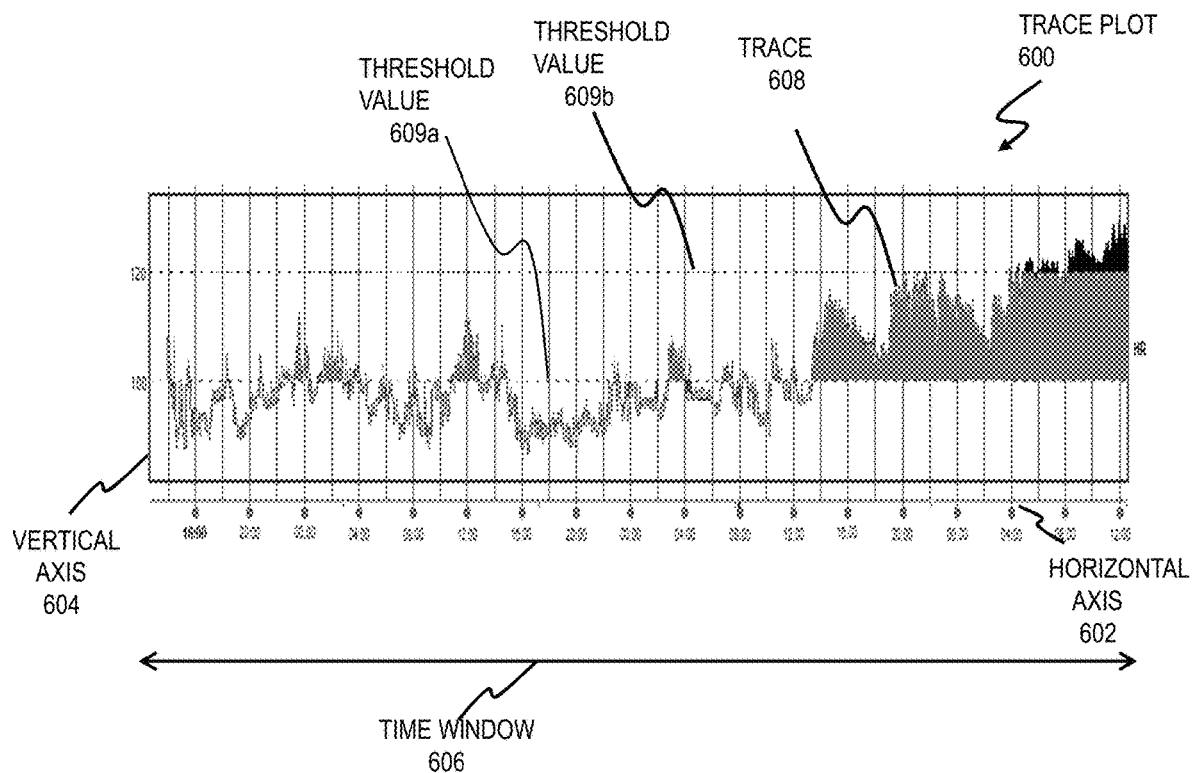
FIG. 6A is an image that illustrates an example of a trace of the trace region of FIG. 5B, according to an embodiment.

FIG. 5E is a block diagram that illustrates an example of the active area 506 of the group view 500 of FIG. 5A, according to an embodiment. In one embodiment, the active area 506 includes a trace region 556 where one or more traces of the values of the parameter of physiological patient data is plotted against time. FIG. 5C is a block diagram that illustrates an example of the trace region 556 of FIG. 5E, according to an embodiment. In one embodiment, the trace region 556 includes a plurality of active areas 557a, 557b, where each active area 557 corresponds to a respective parameter of physiological patient data. In an example embodiment, where there is a limited number of active areas 557a, 557b, parameters of physiological patient data with higher priority are displayed first and parameters of physiological patient data with lower priority are displayed if active areas 557a, 557b remain after the higher priority parameters are displayed. In an example embodiment, a trace plot of the values of a first parameter of physiological patient data against time is presented in the first active area 557a and a trace plot of the values of a second parameter of physiological patient data against time is presented in the second active area 557b. FIG. 6A is an image that illustrates an example of a trace plot 600 of the trace region 556 of FIG. 5C, according to an embodiment. The horizontal axis 602 indicates time in units of (hour:minutes) spanning a 24 hour range from 12:00 PM to 12:00 PM. In other embodiments, the range of the horizontal axis 602 can be selected. In an example embodiment, the range can be selected from a minimum value of about 1 minute to a maximum value based on the plurality of sample times for the stored physiological patient data. The vertical axis 604 indicates the parameter of physiological patient data in relevant units (e.g., beats per minute for heartrate). The trace plot 600 includes a trace 608 of the values of the parameter of physiological patient data over a time window 606 encompassing at least some of the plurality of sample times that the controller 106 receives the values of the parameter of physiological patient data. In an example embodiment, the time window 606 is about 24 hours. In some embodiments, a color of the trace 608 changes from a first color to a second color when the value of the parameter of physiological patient data exceeds each of one or more threshold values 609. In an example embodiment, the color of the trace 600 changes from green to yellow at a first threshold value 609a and from yellow to red when the value 608 of the parameter exceeds a second threshold value 609b. That is the trace has one color at values below each threshold value and a different color at values above the threshold value. In an example embodiment, where the parameter of physiological patient data is heart rate, the first threshold value 609a is 100 beats per minute and the second threshold value 609b is approximately 120 beats per minute. In some embodiments, not only is the trace given and the color appropriate for the value, but areas below the trace and above the first threshold value 609a are filled with the corresponding color, as depicted in FIG. 6A.

One notable advantage of the group view 500 is that a user simultaneously views the traces 600 of each patient in a particular group by viewing the active areas 506a, 506b, 506c, 506d and prioritizes which patients require more time and attention. In an example embodiment, if the traces 600 in active areas 506a, 506b are red colored, whereas the traces 600 in the active areas 506c, 506d are green colored, the user can decide to spend more time with the patients associated with active areas 506a, 506b. This improves the efficiency of physicians and medical staff in the medical facility and improves the quality of care provided to patients that require more time and attention. Because these are active areas, in some embodiments, by selecting the active area corresponding to one unit with a pointing device, an expanded view of a single unit is presented on the display; and, the presentation of other units are reduced, as described below with reference to FIG. 5B.

In some embodiments the values plotted in a trace are the values of an "index" which is an indication of a particular condition of the subject that is a function or two or more physiological parameters. In some example embodiments, the index value is a ratio of a value of a first parameter of physiological patient data to a value of a second parameter of physiological patient data. In an example embodiment, the trace 608 indicates an index value that is of a shock index (SI) that is a ratio of a value of heart rate (HR) to a value of systolic blood pressure (SBP). In another example embodiment, the index value is a value of a brain trauma index (BTI) that is a ratio of a value of intracranial blood pressure (ICP) to a value of cerebral perfusion pressure (CPP).

Figure 6B:
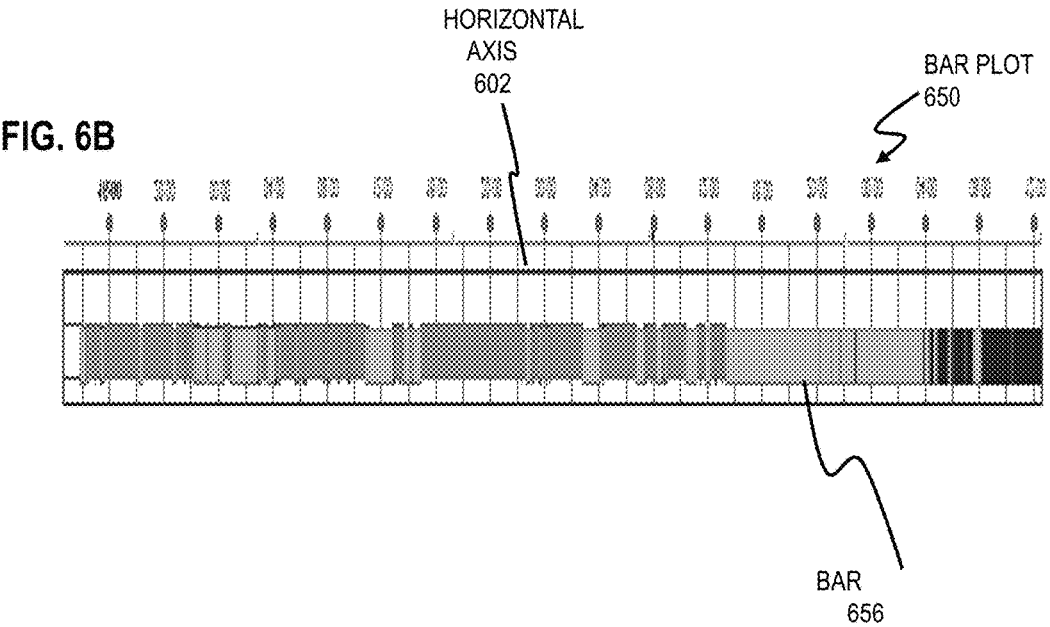
FIG. 6B is an image that illustrates an example of a bar of the bar region of FIG. 5B, according to an embodiment.

In another embodiment, the active area 506 of FIG. 5E includes a bar region 558 where a one dimensional bar plot that indicates a time history of range of the value of the parameter of physiological patient data is displayed as a bar with color that can change along the time axis. FIG. 5D is a block diagram that illustrates an example of the bar region 558 of FIG. 5E, according to an embodiment. In one embodiment, the bar region 558 includes a plurality of active areas 559a, 559b, where each active area 559 corresponds to a respective parameter of physiological patient data. In an example embodiment, a bar plot of the value range of a first parameter of physiological patient data is displayed in the first active area 559a and a bar plot of the value range of a second parameter of physiological patient data is displayed in the second active area 559b. FIG. 6B is an image that illustrates an example of a bar plot 650 of the bar region 558 of FIG. 5D, according to an embodiment. The horizontal axis 602 is time in units of (hour:minutes) spanning a 24 hour range from 12:00 PM to 12:00 PM. In other embodiments, the range of the horizontal axis 602 can be selected. In an example embodiment, the range can be selected from a minimum value of about 1 minute to a maximum value based on the plurality of sample times for the stored physiological patient data. As a one dimensional plot, there is no vertical axis. The bar plot 650 includes a bar 656 that is colored based on the value range of the parameter of physiological patient data over the time window 606. In some embodiments, a color of the bar 656 indicates the value range such that a first color indicates that the range of the value of the parameter of physiological patient data is in a first range (e.g. less than a first threshold value), a second color indicates that the range of the value of the parameter of physiological patient data is in a second range (e.g. greater than the first threshold value but less than a second threshold value) and a third color indicates that the range of the value of the parameter of physiological patient data is in a third range (e.g. greater than the second threshold value). In an example embodiment, the first color is green, the second color is yellow and the third color is red and the first and second thresholds correspond to those used in the trace plot 600 of FIG. 6A. An advantage of the bar plot is that more different physiological parameters can be presented in the same area of the display device because there is no vertical axis. Thus more parameters can be presented per unit in the group. Only one or a few traces can be plotted or only the one or few traces that exceed a first or second threshold are plotted in the trace plot region.

In some embodiments, the value range is a range of a ratio of a value of a first parameter of physiological patient data to a value of a second parameter of physiological patient data. In an example embodiment, the value range is a range of the shock index (SI) or of the brain trauma index (BTI).

Returning to FIG. 5A, in some embodiments, a plurality of active areas 510a, 510b are displayed in a time interval region 508 of the group view 500. In one embodiment, an indicator is displayed in each active area 510, where the indicator is a time interval value. In some embodiments, upon selecting a particular active area 510a by a single action of a pointing device, the interval of the time window 606 of the trace plots 600 in the trace region 556 and the bar plots 650 in the bar region 558 is adjusted based on the time interval value in the particular active area 510a. In one embodiment, the time interval value of the active areas 510 include one or more of 1 hour, 2 hours, 4 hours, 8 hours, 12 hours, 24 hours, 48 hours and 72 hours.

In some embodiments, the group view 500 includes a particular arrangement where the group region 502 is presented on a left side of the display 108, the time region 508 is presented in a bottom portion of the display and the unit region 505 is presented to a right side of the group region 502 and above the time region 508. However, this is merely one example arrangement and other embodiments of the group view 500 can feature different rearrangements of the group region 502, time region 108 and unit region 505.

FIG. 7B is a flow diagram that illustrates an example of a method 720 for displaying the group view 500 of physiological data collected from the plurality of bed units 102 divided into groups in a medical facility, according to an embodiment. In step 722, the value of the parameter of physiological patient data and the value of the sample time is received at the controller 106. In some embodiments, the value of the parameter of physiological patient data and the value of the sample time is received at the controller 106 from each server 105. In other embodiments, the value of the parameter of physiological patient data and the value of the sample time is received from the plurality of physiological data monitors 104 associated with the plurality of bed units 102 divided into the one or more groups of the medical facility without use of the server or the controller.

In step 724, indicators in the active areas 504 of the group region 502 are presented, where each active area 504 corresponds to a respective group within the medical facility. In some embodiments, where a fixed number of active areas 506 are provided in the unit region 505 and the number of bed units 102 within a particular group exceeds the fixed number, multiple active areas 504 correspond to the respective group within the medical facility.

In step 726, data is received based on a selection of a particular active area 504a of the group region 502. In an embodiment, the particular active area 504a of the group region 502 is selected by a single or other action of a pointing device. In one embodiment, the display 108 is a touchscreen and the single action of the pointing device involves touching the particular active area 504a. In an example embodiment, the particular active area 504a is selected in order to monitor the values of the parameter of physiological patient data of bed units 102 in the group corresponding to the particular active area 504a. In an embodiment, in step 726, the controller 106 receives a signal from the display 108 based on the selection of the particular active area 504a of the group region 502.

In step 728, a representation based on the value of the parameter of physiological patient data is displayed in the active areas 506 of the unit region 505, where each active area 506 corresponds to a respective bed unit 102 within the group that corresponds to the particular active area 504a selected in step 726. In some embodiments, in step 728, the trace plot 600 of the trace 608 of the parameter values against time of the physiological patient data is displayed in the trace region 556 of the active area 506. In an example embodiment, in step 728, multiple trace plots 600 are displayed in multiple active areas 557a, 557b of the trace region 556, where each trace plot 600 in each active area 557 corresponds to a respective parameter of physiological patient data.

In some embodiments, in step 728, the bar plot 650 of the parameter of the physiological patient data is displayed in the bar region 558 of the active area 506. In an example embodiment, in step 728, multiple bar plots 650 are displayed in multiple active areas 559a, 559b of the bar region 558, where each bar plot 650 in each active area 559 corresponds to a respective parameter of physiological patient data.

In one embodiment, in response to a selection by a single or other action of a pointing device within a particular unit active area 506a in the group view 500, the value of the physiological patient data for the bed unit 102 corresponding to the particular active area 506a is displayed in a different screen called unit view 550. FIG. 5B is a block diagram that illustrates an example of the unit view 550 for displaying physiological patient data, according to an embodiment. In one embodiment, the unit view 550 includes an indicator in a plurality of active areas 554a, 554b in a thumbnail region 552. In some embodiments, each active area 554 corresponds to a respective bed unit 102 within the group corresponding to the selected active area 504a in the group view 500. In some embodiments, the indicator in each active area 554 is a thumbnail image of the traces and bars presented in the active area 506 of the unit region 505 corresponding to the respective bed unit 102.

The unit view 550 further includes the trace region 556 with the plurality of active areas 557 (FIG. 5C), where each active area 557 corresponds to a respective parameter of physiological patient data. In an embodiment, the trace plot 600 of the trace 608 of the parameter of physiological patient data is displayed in the active area 557 of the trace region 556, where the physiological patient data corresponds to the bed unit 102 associated with the particular active area 506a selected in the group view 500.

Additionally, the unit view 550 includes the bar region 558 with the plurality of active areas 559 (FIG. 5D), where each active area 559 corresponds to a respective parameter of physiological patient data. In an embodiment, the bar plot 650 of the bar of colored or cross-hatched value ranges of the parameter of physiological patient data is displayed in each active area 559 of the bar region 558, where the physiological patient data corresponds to the bed unit 102 associated with the particular active area 506a selected in the group view 500.

In other embodiments, in response to a selection by a single or other action of a pointing device within a particular active area 554a in the thumbnail region 552, the value of the physiological patient data for the bed unit 102 corresponding to the particular active area 554a is displayed in the unit view 550.

In one embodiment, the unit view 550 further includes one or more active areas 562a, 562b in an index region 560. In one embodiment, a scatter index plot rather than a time series is presented in each active area 562. In a scatter plot, data points are plotted based on a value of a first parameter of physiological patient data on one axis and a value of a second parameter of physiological patient data on the perpendicular axis. In an example embodiment, the index plot is a shock index (SI) plot where the first parameter of physiological patient data is heart rate (HR) and the second parameter of physiological patient data is systolic blood pressure (SBP). In another example embodiment, the index plot is a brain trauma index (BTI) plot, where the first parameter of physiological patient data is intracranial blood pressure (ICP) and the second parameter of physiological patient data is cerebral perfusion pressure (CPP). FIG. 6C is an image that illustrates an example of an index plot 670 of the index region 560 of FIG. 5B, according to an embodiment. The horizontal axis 672 is a first parameter of physiological patient data (e.g. heartrate) in units of the parameter (e.g. beats per minute) in a range from about 80 beats per minute to about 138 beats per minute. The vertical axis 674 is a second parameter of physiological patient data (e.g. systolic blood pressure, SBP) in units of the parameter (e.g. millimeters of Mercury). In some embodiments, a range of the second parameter of physiological patient data is dynamically determined by minimum and maximum values acquired over the time window 606. In some embodiments, the index plot 670 includes data points 682 that have coordinates (x, y) where x is a value of the first parameter of physiological patient data along the horizontal axis 672 and y is a value of the second parameter of physiological patient data along the vertical axis 674. In some embodiments, the index plot 670 includes a color coded time axis 676 such that a sample time of each data point 682 can be color coded according to the color coded time axis 676. The time window 606 defines the range of the coded time axis 676. In an example embodiment, the time window 606 is about 24 hours. In one embodiment, the coded time axis 676 is a color coded time axis and each data point 682 is color coded based on the respective sample time of each data point 682 and the color coded time axis 676. In an example embodiment, the color coded time axis 676 is a color spectrum that extends from a red color to designate more recent sample times to a blue color to indicate earlier sample times. In this example embodiment, the data points 682 during recent sample times are color coded red whereas the data points 682 during previous sample times are color coded blue. FIG. 6C depicts lines that correlate color coded portions of the time axis 676 and respective data points 682 of the plot 670.

As illustrated in FIG. 6C, in one embodiment the index plot 670 includes one or more vertical intercept lines 678 that intersect the horizontal axis 672 to indicate one or more respective threshold values of the first parameter of physiological patient data. In another embodiment, the index plot 670 includes one or more horizontal intercept lines 680 that intersect the vertical axis 674 to indicate one or more respective threshold values of the second parameter of physiological patient data. The vertical intercept lines 678 and horizontal intercept lines 680 advantageously allow the user to determine whether data points 682 are within a region of the plot 670 defined by the intercept lines 678, 680. In an example embodiment, where the index plot 670 is a shock index (SI) plot, the intercept lines 678, 680 allow the user to determine whether the data points 682 are within a region of concern 673 defined by a vertical intercept line 678 and horizontal intercept line 680. In another example embodiment, the color coded points 682 based on the time axis 676 advantageously permit the user to determine whether the points 682 are trending toward the region of concern 673.

As illustrated in FIG. 5B, in one embodiment the unit view 550 further includes a plurality of active areas 570*a*, 570*b* in an action region 568. In an embodiment, an action indicator is displayed in each active area 570*a*, 570*b*. In one embodiment, in response to selection of the active area 570*a* by a single or other action of a pointing device, an image file of the unit view 550 is generated and stored in a memory of the controller 106. In one embodiment, the image file of the unit view 550 represents an image of the thumbnail region 552, the trace region 556, the bar region 558 and the index region 560 at the time that the active area 570*a* is selected. In an example embodiment, the action indicator in the active area 570*a* is "snapshot".

In one embodiment, in response to selection of the active area 570*b* by a single or other action of a pointing device, the value of a waveform parameter of physiological patient data is displayed over a secondary time window 606' that is less than the time window 606. In some embodiments, the value of the waveform parameter of physiological patient data is provided to the server 105 by the waveform generators 156*a*, 156*b*, 156*c*. This option is useful for traces that are better viewed on a much expanded time axis, such as an EKG. FIG. 6D is an image that illustrates an example trace plot 600' of a trace 608' of values of a waveform parameter of physiological patient data, according to an embodiment. In this embodiment, the parameter of physiological patient data is an EKG waveform parameter of physiological patient data. In an embodiment, the value of the waveform parameter of physiological patient data is displayed in one of the active areas 557 of the trace region 556. In an example embodiment, the waveform parameter of physiological patient data is an electrocardiographic (EKG) or a photoplethysmographic (PPG). In another example embodiment, the secondary time window 606' is less than 1 hour. In another example embodiment, the secondary time window 606' is less than 10 minutes.

In some embodiments, the time window 606 of the traces 600 in the trace region 556, the bars 650 in the bar region 558 and the index plot 670 in the index region 560 can be adjusted. In one embodiment, the time window 606 is adjusted by selecting an active area 566*a*, 566*b* in a time interval region 564 of the unit view 550, where each active area 566 includes a time interval value. Upon selecting a particular active area 566*a*, the time window 606 is adjusted based on the time interval value within the particular active area 566*a*. In one embodiment, the time interval value of the active areas 566 include one or more of 1 hour, 2 hours, 4 hours, 8 hours, 12 hours, 24 hours, 48 hours and 72 hours. In another embodiment, the time window 606 is adjusted by manually selecting a secondary time window within the time window 606 by a single action of a pointing device. In response to this manual selection of the secondary window within the time window 606, the trace plots 600 in the trace region 556, bar plots 650 in the bar region 558 and index plot 670 in the index region 560 are displayed over the secondary time window.

In some embodiments, highlighting one or more areas (e.g. moving cursor to one or more areas with the pointing device 816 such as a mouse) along one or more of the trace 600, the bar plot 650 and/or the index plot 670, generates an output on the display of a value of the respective trace/bar plot/index plot and/or a value of the time associated with the highlighted trace/bar plot/index plot value. In one embodiment, highlighting the one or more areas further displays a vertical line along the trace/bar plot/index plot at the respective time value.

In some embodiments, the unit view 550 further includes a home region 572 with an active area 574. In one embodiment, an indicator is displayed in the active area 574. In an example embodiment, the indicator is a home symbol. Upon selecting the active area 574 by a single or other action of a pointing device, the display 108 switches from the unit view 550 of FIG. 5B to the group view 500 of FIG. 5A.

FIG. 7C is a flow diagram that illustrates an example of a method 730 for displaying the unit view 550 of physiological data collected from the plurality of bed units 102 in a medical facility, according to an embodiment. In step 732, the value of the parameter of physiological patient data and the value of the sample time is received at the controller 106 from the plurality of physiological data monitors 104. In some embodiments, in step 732, the value of the parameter of physiological patient data and the value of the sample time is received at the controller 106 from the servers 105, which in turn received the data from the plurality of physiological data monitors 104.

In step 734, an indicator is displayed in the active areas 554 of the thumbnail region 552 of the unit view 550, where each active area 554 corresponds to a respective bed unit 102. In some embodiments, each active area 554 corresponds to a respective bed unit 102 in the group associated with the selected active area 504 in the group region 502 of the group view 500. In some embodiments, the indicator in each active area 554 is the active area 506 of the unit region 505 corresponding to the respective bed unit 102.

In step 736, the trace plot 600 including the trace 608 of the value of the parameter of the physiological patient data is displayed in the active areas 557 of the trace region 556, where each active area 557 corresponds to a respective parameter of physiological patient data. In some embodiments, in step 736, the trace 600 is a value of an index parameter based on a function, such as a ratio, of a value of a first parameter of physiological patient data and a value of a second parameter of physiological patient data.

In step 738, the bar plot 650 including that the bar 656 that indicates a range of the value of the parameter of the physiological patient data is displayed in the active areas 559 of the bar region 558, where each active area 559 corresponds to a respective parameter of physiological patient data. In some embodiments, in step 738, the bar 656 color indicates a value range of an index parameter based on a ratio of a value of a first parameter of physiological patient data to a value of a second parameter of physiological patient data.

In step 740, one or more scatter index plots 670 are displayed in the active areas 562 of the index region 560, where each active area 562 corresponds to a respective index plot 670 of a respective index parameter of physiological patient data. In an embodiment, the index parameter is shock index (SI) or brain trauma index (BTI). Data points 682 of the index plot 670 are presented, where each data point 682 is based on a value of a first parameter of physiological patient data and a value of a second parameter of physiological patient data. In some embodiments, the data points 682 of the index plot 670 have (x, y) coordinates, where x is the value of the first parameter of physiological patient data and y is the value of the second parameter of physiological patient data.

In some embodiments, based on the physiological patient data received at the controller 106, any predictive algorithm known in the art could be used to make a prediction regarding future physiological patient data or recommend treatment of the patient. In an example embodiment, such a prediction or recommendation could be presented on the screen view presented on any display 108. An example of such a predictive algorithm is disclosed in Provisional Application No. 62/334,750 filed on May 11, 2016 and with a common assignee with the present invention.

2. Example Embodiments

In one embodiment, the system 100, 150 is utilized and/or the method 700, 720, 730 is practiced in a military medical transport facility, such as a military medical transport vehicle. Conventional military medical transport vehicles routinely feature limited medical staff and thus involve limited access to patients and equipment instability (e.g. data monitors 104 and severs 105) in a noisy and moving environment. Additionally, conventional military medical transport vehicles do not feature remote monitoring of current values of the parameter of physiological patient data from the data monitors 104. The implementation of the system 100, 150 and/or the method 700, 720, 730 in military medical transport vehicles addresses these issues by permitting the limited medical staff to monitor more patients in a shorter amount of time and/or to quickly detect and remedy any equipment instability.

In one embodiment, the controller 106 of the system 100, 150 is an Intel i5 1.9 GHz CPU with 16 GB memory and running on Windows 7 operating system. In an example embodiment, 16 units 102 are provided at the medical facility and 16 data monitors 104 are provided at each unit 102 to provide values for 16 parameters of physiological patient data. In this example embodiment, where the data monitors 104 provide parameter values at each minute, the controller 106 receives about 0.37 million data points over a 24 hour period. In an embodiment, such daily amounts of data can be displayed in real-time or near real-time (e.g. <1 second or <0.5 seconds or <250 milliseconds) in the block 300 and/or the gap collection pattern 400 and/or the group view 500 and/or the unit view 550. Table 2 below depicts that the update time of the block 300 and/or pattern 400 and/or group view 500 and/or unit view 550 is on the order of hundreds of milliseconds (e.g. <500 milliseconds) for physiological patient data that is updated each minute.

TABLE 2

| Self | | Total | | Function | |
|---|---|---|---|---|---|
| 15319.5 ms | | 15319.5 ms | | (idle) | |
| 196.4 ms | 34.57% | 196.4 ms | 34.57% | (program) | |
| 118.3 ms | 20.82% | 229.2 ms | 40.33 | drawUnitData | 10.14.1.23/:269 |
| 30.6 ms | 5.39% | 70.8 ms | 12.45% | drawOneData | 10.14.1.23/:1029 |
| 29.6 ms | 5.20% | 107.7 ms | 18.96% | $.ajax.success | 10.14.1.23/:1553 |
| 26.4 ms | 4.65% | 193.3 ms | 34.01% | $.ajax.success | 10.14.1.23/:1573 |
| 23.2 ms | 4.09% | 23.2 ms | 4.09% | lineTo | |
| 15.8 ms | 2.79% | 15.8 ms | 2.79% | (anonymous function) | |
| 14.8 ms | 2.60% | 166.9 ms | 29.37% | drawSideGroupData | 10.14.1.23/:1424 |
| 14.8 ms | 2.60% | 14.8 ms | 2.60% | (garbage collector) | |
| 11.6 ms | 2.04% | 11.6 ms | 2.04% | parseDataTime | 10.14.1.23/:224 |
| 6.3 ms | 1.12% | 6.3 ms | 1.12% | fillText | |
| 5.3 ms | 0.93% | 19.0 ms | 3.35% | drawDataOverView | 10.14.1.23/:729 |
| 5.3 ms | 0.93% | 5.3 ms | 0.93% | fillRect | |
| 4.2 ms | 0.74% | 4.2 ms | 0.74% | measureText | |

In an embodiment, the system and method discussed herein has the capacity to deliver a remote patient monitoring platform refined and customized for use in the medical transport setting. In one embodiment, the system and method discussed herein provides both remote and on-board clinicians with the capability to simultaneously monitor dynamic physiologic changes in multiple patients. This offers the ability to identify critically worsening patients quickly and more effectively as both current and trend data can be clearly displayed. This technology allows for integration with clinical decision support tailored to the individual patient, providing unprecedented help in the austere battlefield environment. Traumatic brain injuries are common in the military population and reliable remote monitoring allows specialists to aid in the critical early hours of treatment of these complex injuries.

In an embodiment, the system and method discussed herein is practiced in a medical facility including 94 bed units 102 with 94 data monitors 104 (e.g. GE-Marquette Solar 7000/8000®, General Electric, Fairfield Conn.). In one embodiment, the 94 data monitors 104 are networked to provide collection of real time physiological patient data including 13 data monitors 104 in a trauma resuscitation unit (TRU); 9 data monitors 104 in an operating room (OR); 12 data monitors 104 in a post-anesthesia care unit (PACU) and 60 data monitors 104 in an intensive care unit (ICU). In an example embodiment, each data monitor 104 collects real-time 240 Hz waveforms (e.g. ECG, PPG, CO2, ABP, ICP) and 0.5 Hz trend data (e.g. HR, RR, SpO2, CO2, ICP) which are broadcasted via UDP (User Datagram Protocol) through secure intranet to a dedicated server 105c (e.g. Bedmaster® with Excel Medical Electronics, Jupiter Fla.). In the example embodiment, about 20 million data points per unit 102 are generated each day or roughly 30 terabits per year of data. During a twelve month study from February 2013 to January 2014, a total of 8719 adult patients stayed in the medical facility for an average stay of 3.8 days. In an example embodiment, collection rates from each individual server 105 were in a range from between 27.79% and 40.49% prior to implementing the system 100, 150. In an example embodiment, after implementation of the triple redundant server system (e.g. servers 105 connected in the triple redundant arrangement) but before the implementation of the system 100, 150 the data collection rate improved to about 79.13%. In an example embodiment, the missing collection rate (gap) was about 20.87% and was mostly due to collection gaps of greater than 4 hours (e.g. 18.02% or 1.62 times per bed per month) and collection gaps of between 5 minutes and 4 hours (e.g. 0.13% or 0.6 times per bed per month). In an example embodiment, reasons for collection gaps included individual collection server failure, software instability, individual bed setting consistency and/or clinical engineering servicing of patient monitors. In an example embodiment, in a 6 month period after implementation of the system 100, 150, the single server collection rate improved to a range between 87.05% and 95.54% and the triple redundant system achieved 99.88% total collection rate. Table 3 below depicts the server collection rates for the individual and combined server arrangements before and after implementation of the system 100, 150 ("pre-MoMs", "post-MoMs").

TABLE 3

|  | Server 1 collected | Server 2 collected | Server 3 collected | Server 3 contributed | Server 1 contributed | Combined |
|---|---|---|---|---|---|---|
| Pre-MoMs | 40.5% | 27.8% | 36.3% | 25.4% | 26.0% | 79.1% |
| Post-MoMs | 95.4% | 95.5% | 87.1% | 4.2% | 0.2% | 99.9% |

3. Hardware Overview

FIG. 8 is a block diagram that illustrates a computer system 800 upon which an embodiment of the invention may be implemented. Computer system 800 includes a communication mechanism such as a bus 810 for passing information between other internal and external components of the computer system 800. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 800, or a portion thereof, constitutes a means for performing one or more steps of one or more methods described herein.

A sequence of binary digits constitutes digital data that is used to represent a number or code for a character. A bus 810 includes many parallel conductors of information so that information is transferred quickly among devices coupled to the bus 810. One or more processors 802 for processing information are coupled with the bus 810. A processor 802 performs a set of operations on information. The set of operations include bringing information in from the bus 810 and placing information on the bus 810. The set of operations also typically include comparing two or more units of information, shifting positions of units of information, and combining two or more units of information, such as by addition or multiplication. A sequence of operations to be executed by the processor 802 constitutes computer instructions.

Computer system 800 also includes a memory 804 coupled to bus 810. The memory 804, such as a random access memory (RAM) or other dynamic storage device, stores information including computer instructions. Dynamic memory allows information stored therein to be changed by the computer system 800. RAM allows a unit of information stored at a location called a memory address to be stored and retrieved independently of information at neighboring addresses. The memory 804 is also used by the processor 802 to store temporary values during execution of computer instructions. The computer system 800 also includes a read only memory (ROM) 806 or other static storage device coupled to the bus 810 for storing static information, including instructions, that is not changed by the computer system 800. Also coupled to bus 810 is a non-volatile (persistent) storage device 808, such as a magnetic disk or optical disk, for storing information, including instructions, that persists even when the computer system 800 is turned off or otherwise loses power.

Information, including instructions, is provided to the bus 810 for use by the processor from an external input device 812, such as a keyboard containing alphanumeric keys operated by a human user, or a sensor. A sensor detects conditions in its vicinity and transforms those detections into signals compatible with the signals used to represent information in computer system 800. Other external devices coupled to bus 810, used primarily for interacting with humans, include a display device 814, such as a cathode ray tube (CRT) or a liquid crystal display (LCD), for presenting images, and a pointing device 816, such as a mouse or a trackball or cursor direction keys, for controlling a position of a small cursor image presented on the display 814 and issuing commands associated with graphical elements presented on the display 814.

In the illustrated embodiment, special purpose hardware, such as an application specific integrated circuit (IC) 820, is coupled to bus 810. The special purpose hardware is configured to perform operations not performed by processor 802 quickly enough for special purposes. Examples of application specific ICs include graphics accelerator cards for generating images for display 814, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 800 also includes one or more instances of a communications interface 870 coupled to bus 810. Communication interface 870 provides a two-way communication coupling to a variety of external devices that operate with their own processors, such as printers, scanners and external disks. In general the coupling is with a network link 878 that is connected to a local network 880 to which a variety of external devices with their own processors are connected. For example, communication interface 870 may be a parallel port or a serial port or a universal serial bus (USB) port on a personal computer. In some embodiments, communications interface 870 is an integrated services digital network (ISDN) card or a digital subscriber line (DSL) card or a telephone modem that provides an information communication connection to a corresponding type of telephone line. In some embodiments, a communication interface 870 is a cable modem that converts signals on bus 810 into signals for a communication connection over a coaxial cable or into optical signals for a communication connection over a fiber optic cable. As another example, communications interface 870 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 870 sends and receives electrical, acoustic or electromagnetic signals, including infrared and optical signals, that carry information streams, such as digital data.

The term computer-readable medium is used herein to refer to any medium that participates in providing information to processor 802, including instructions for execution. Such a medium may take many forms, including, but not limited to, non-volatile media, volatile media and transmission media. Non-volatile media include, for example, optical or magnetic disks, such as storage device 808. Volatile media include, for example, dynamic memory 804. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 802, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 802, except for carrier waves and other signals.

Logic encoded in one or more tangible media includes one or both of processor instructions on a computer-readable storage media and special purpose hardware, such as ASIC *820.

Network link 878 typically provides information communication through one or more networks to other devices that use or process the information. For example, network link 878 may provide a connection through local network 880 to a host computer 882 or to equipment 884 operated by an Internet Service Provider (ISP). ISP equipment 884 in turn provides data communication services through the public, world-wide packet-switching communication network of networks now commonly referred to as the Internet 890. A computer called a server 892 connected to the Internet provides a service in response to information received over the Internet. For example, server 892 provides information representing video data for presentation at display 814.

The invention is related to the use of computer system 800 for implementing the techniques described herein. According to one embodiment of the invention, those techniques are performed by computer system 800 in response to processor 802 executing one or more sequences of one or more instructions contained in memory 804. Such instructions, also called software and program code, may be read into memory 804 from another computer-readable medium such as storage device 808. Execution of the sequences of instructions contained in memory 804 causes processor 802 to perform the method steps described herein. In alternative embodiments, hardware, such as application specific integrated circuit 820, may be used in place of or in combination with software to implement the invention. Thus, embodiments of the invention are not limited to any specific combination of hardware and software.

The signals transmitted over network link 878 and other networks through communications interface 870, carry information to and from computer system 800. Computer system 800 can send and receive information, including program code, through the networks 880, 890 among others, through network link 878 and communications interface 870. In an example using the Internet 890, a server 892 transmits program code for a particular application, requested by a message sent from computer 800, through Internet 890, ISP equipment 884, local network 880 and communications interface 870. The received code may be executed by processor 802 as it is received, or may be stored in storage device 808 or other non-volatile storage for later execution, or both. In this manner, computer system 800 may obtain application program code in the form of a signal on a carrier wave.

Various forms of computer readable media may be involved in carrying one or more sequence of instructions or data or both to processor 802 for execution. For example, instructions and data may initially be carried on a magnetic disk of a remote computer such as host 882. The remote computer loads the instructions and data into its dynamic memory and sends the instructions and data over a telephone line using a modem. A modem local to the computer system 800 receives the instructions and data on a telephone line and uses an infra-red transmitter to convert the instructions and data to a signal on an infra-red a carrier wave serving as the network link 878. An infrared detector serving as communications interface 870 receives the instructions and data carried in the infrared signal and places information representing the instructions and data onto bus 810. Bus 810 carries the information to memory 804 from which processor 802 retrieves and executes the instructions using some of the data sent with the instructions. The instructions and data received in memory 804 may optionally be stored on storage device 808, either before or after execution by the processor 802.

FIG. 9 illustrates a chip set 900 upon which an embodiment of the invention may be implemented. Chip set 900 is programmed to perform one or more steps of a method described herein and includes, for instance, the processor and memory components described with respect to FIG. 8 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 900, or a portion thereof, constitutes a means for performing one or more steps of a method described herein.

In one embodiment, the chip set 900 includes a communication mechanism such as a bus 901 for passing information among the components of the chip set 900. A processor 903 has connectivity to the bus 901 to execute instructions and process information stored in, for example, a memory 905. The processor 903 may include one or more processing cores with each core configured to perform independently. A multi-core processor enables multiprocessing within a single physical package. Examples of a multi-core processor include two, four, eight, or greater numbers of processing cores. Alternatively or in addition, the processor 903 may include one or more microprocessors configured in tandem via the bus 901 to enable independent execution of instructions, pipelining, and multithreading. The processor 903 may also be accompanied with one or more specialized components to perform certain processing functions and tasks such as one or more digital signal processors (DSP) 907, or one or more application-specific integrated circuits (ASIC) 909. A DSP 907 typically is configured to process real-world signals (e.g., sound) in real time independently of the processor 903. Similarly, an ASIC 909 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 903 and accompanying components have connectivity to the memory 905 via the bus 901. The memory 905 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 905 also stores the data associated with or generated by the execution of one or more steps of the methods described herein.

FIG. 10 is a diagram of exemplary components of a mobile terminal 1000 (e.g., cell phone handset) for communications, which is capable of operating in the system of FIG. 2C, according to one embodiment. In some embodiments, mobile terminal 1001, or a portion thereof, constitutes a means for performing one or more steps described herein. Generally, a radio receiver is often defined in terms of front-end and back-end characteristics. The front-end of the receiver encompasses all of the Radio Frequency (RF) circuitry whereas the back-end encompasses all of the base-band processing circuitry. As used in this application, the term "circuitry" refers to both: (1) hardware-only implementations (such as implementations in only analog and/or digital circuitry), and (2) to combinations of circuitry and software (and/or firmware) (such as, if applicable to the particular context, to a combination of processor(s), including digital signal processor(s), software, and memory(ies) that work together to cause an apparatus, such as a mobile phone or server, to perform various functions). This definition of "circuitry" applies to all uses of this term in this application, including in any claims. As a further example, as used in this application and if applicable to the particular context, the term "circuitry" would also cover an implementation of merely a processor (or multiple processors) and its (or their) accompanying software/or firmware. The term "circuitry" would also cover if applicable to the particular context, for example, a baseband integrated circuit or applications processor integrated circuit in a mobile phone or a similar integrated circuit in a cellular network device or other network devices.

Pertinent internal components of the telephone include a Main Control Unit (MCU) 1003, a Digital Signal Processor (DSP) 1005, and a receiver/transmitter unit including a microphone gain control unit and a speaker gain control unit. A main display unit 1007 provides a display to the user in support of various applications and mobile terminal functions that perform or support the steps as described herein. The display 1007 includes display circuitry configured to display at least a portion of a user interface of the mobile terminal (e.g., mobile telephone). Additionally, the display 1007 and display circuitry are configured to facilitate user control of at least some functions of the mobile terminal. An audio function circuitry 1009 includes a microphone 1011 and microphone amplifier that amplifies the speech signal output from the microphone 1011. The amplified speech signal output from the microphone 1011 is fed to a coder/decoder (CODEC) 1013.

A radio section 1015 amplifies power and converts frequency in order to communicate with a base station, which is included in a mobile communication system, via antenna 1017. The power amplifier (PA) 1019 and the transmitter/modulation circuitry are operationally responsive to the MCU 1003, with an output from the PA 1019 coupled to the duplexer 1021 or circulator or antenna switch, as known in the art. The PA 1019 also couples to a battery interface and power control unit 1020.

In use, a user of mobile terminal 1001 speaks into the microphone 1011 and his or her voice along with any detected background noise is converted into an analog voltage. The analog voltage is then converted into a digital signal through the Analog to Digital Converter (ADC) 1023. The control unit 1003 routes the digital signal into the DSP 1005 for processing therein, such as speech encoding, channel encoding, encrypting, and interleaving. In one embodiment, the processed voice signals are encoded, by units not separately shown, using a cellular transmission protocol such as enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., microwave access (WiMAX), Long Term Evolution (LTE) networks, code division multiple access (CDMA), wideband code division multiple access (WCDMA), wireless fidelity (WiFi), satellite, and the like, or any combination thereof.

The encoded signals are then routed to an equalizer 1025 for compensation of any frequency-dependent impairments that occur during transmission though the air such as phase and amplitude distortion. After equalizing the bit stream, the modulator 1027 combines the signal with a RF signal generated in the RF interface 1029. The modulator 1027 generates a sine wave by way of frequency or phase modulation. In order to prepare the signal for transmission, an up-converter 1031 combines the sine wave output from the modulator 1027 with another sine wave generated by a synthesizer 1033 to achieve the desired frequency of transmission. The signal is then sent through a PA 1019 to increase the signal to an appropriate power level. In practical systems, the PA 1019 acts as a variable gain amplifier whose gain is controlled by the DSP 1005 from information received from a network base station. The signal is then filtered within the duplexer 1021 and optionally sent to an antenna coupler 1035 to match impedances to provide maximum power transfer. Finally, the signal is transmitted via antenna 1017 to a local base station. An automatic gain control (AGC) can be supplied to control the gain of the final stages of the receiver. The signals may be forwarded from there to a remote telephone which may be another cellular telephone, any other mobile phone or a land-line connected to a Public Switched Telephone Network (PSTN), or other telephony networks.

Voice signals transmitted to the mobile terminal 1001 are received via antenna 1017 and immediately amplified by a low noise amplifier (LNA) 1037. A down-converter 1039 lowers the carrier frequency while the demodulator 1041 strips away the RF leaving only a digital bit stream. The signal then goes through the equalizer 1025 and is processed by the DSP 1005. A Digital to Analog Converter (DAC) 1043 converts the signal and the resulting output is transmitted to the user through the speaker 1045, all under control of a Main Control Unit (MCU) 1003 which can be implemented as a Central Processing Unit (CPU) (not shown).

The MCU 1003 receives various signals including input signals from the keyboard 1047. The keyboard 1047 and/or the MCU 1003 in combination with other user input components (e.g., the microphone 1011) comprise a user interface circuitry for managing user input. The MCU 1003 runs a user interface software to facilitate user control of at least some functions of the mobile terminal 1001 as described herein. The MCU 1003 also delivers a display command and a switch command to the display 1007 and to the speech output switching controller, respectively. Further, the MCU 1003 exchanges information with the DSP 1005 and can access an optionally incorporated SIM card 1049 and a memory 1051. In addition, the MCU 1003 executes various control functions required of the terminal. The DSP 1005 may, depending upon the implementation, perform any of a variety of conventional digital processing functions on the voice signals. Additionally, DSP 1005 determines the background noise level of the local environment from the signals detected by microphone 1011 and sets the gain of microphone 1011 to a level selected to compensate for the natural tendency of the user of the mobile terminal 1001.

The CODEC 1013 includes the ADC 1023 and DAC 1043. The memory 1051 stores various data including call incoming tone data and is capable of storing other data including music data received via, e.g., the global Internet. The software module could reside in RAM memory, flash memory, registers, or any other form of writable storage medium known in the art. The memory device 1051 may be, but not limited to, a single memory, CD, DVD, ROM, RAM, EEPROM, optical storage, magnetic disk storage, flash memory storage, or any other non-volatile storage medium capable of storing digital data.

An optionally incorporated SIM card 1049 carries, for instance, important information, such as the cellular phone number, the carrier supplying service, subscription details, and security information. The SIM card 1049 serves primarily to identify the mobile terminal 1001 on a radio network. The card 1049 also contains a memory for storing a personal telephone number registry, text messages, and user specific mobile terminal settings.

In some embodiments, the mobile terminal 1001 includes a digital camera comprising an array of optical detectors, such as charge coupled device (CCD) array 1065. The output of the array is image data that is transferred to the MCU for further processing or storage in the memory 1051 or both. In the illustrated embodiment, the light impinges on the optical array through a lens 1063, such as a pin-hole lens or a material lens made of an optical grade glass or plastic material. In the illustrated embodiment, the mobile terminal 1001 includes a light source 1061, such as a LED to illuminate a subject for capture by the optical array, e.g., CCD 1065. The light source is powered by the battery interface and power control module 1020 and controlled by the MCU 1003 based on instructions stored or loaded into the MCU 1003.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article. As used herein, unless otherwise clear from the context, a value is "about" another value if it is within a factor of two (twice or half) of the other value. While example ranges are given, unless otherwise clear from the context, any contained ranges are also intended in various embodiments. Thus, a range from 0 to 10 includes the range 1 to 4 in some embodiments.

What is claimed is:

1. A method implemented on a processor for automatic operation, the method comprising:

for each of a plurality of sample times, receiving, on a processor, a value of at least one parameter of subject condition data and a value of each sample time from at least one server, where the value of the at least one parameter of subject condition data and the value of each sample time is received on the at least one server from a plurality of subject condition data monitors associated with a respective plurality of units in a facility;

for a current sample time, storing, in a data structure, the subject condition data from each unit, said data structure including a first field for holding data indicating the current sample time and a second field for holding data indicating a value of the at least one parameter of the subject condition data;

for the current sample time, determining, on the processor, a time gap defined by a duration between the current sample time and a most recent sample time;

for the current sample time, determining, on the processor, whether the time gap for at least one unit of the plurality of units exceeds at least one time gap threshold; and for the current sample time, causing an apparatus to perform a remedial action based on the determining whether the time gap exceeds the at least one time gap threshold.

2. The method of claim 1, wherein the causing step comprises presenting, on a display, an indicator for each unit.

3. The method of claim 2, wherein the indicator is a color-coded indicator.

4. The method of claim 3, wherein the at least one time gap threshold includes a first time gap threshold and a second time gap threshold that is greater than the first time gap threshold;

and wherein the determining whether the time gap exceeds the at least one time gap threshold comprises at least one of:

determining that the time gap is less than the first time gap threshold, wherein the color-coded indicator is a green indicator;

determining that the time gap exceeds the first time gap threshold and is less than the second time gap threshold, wherein the color-coded indicator is a yellow indicator; and determining that the time gap exceeds the second time gap threshold, wherein the color-coded indicator is a red indicator.

5. The method of claim 2, wherein the indicator comprises the time gap.

6. The method of claim 1, wherein the parameter of subject condition data is at least one of electrocardiographic (ECG), photoplethysmographic (PPG), carbon dioxide (CO2), arterial blood pressure (ABP), intracranial pressure (ICP), heart rate (HR), respiratory rate (RR), temperature, oxygen saturation (SP02) and end-tidal CO2 (EtCO2).

7. The method of claim 2, wherein the data structure includes a third field for holding data indicating the at least one parameter of the subject condition data, wherein the indicator is a color-coded indicator based on at least one of the second field data and the third field data of the data structure.

8. The method of claim 7, wherein the color-coded indicator is other than a green indicator, a yellow indicator and a red indicator.

9. The method of claim 2, wherein the step of receiving, on the processor, further comprises receiving a plurality of identifiers for the respective plurality of units and wherein said storing further comprises storing the identifier of each unit in the data structure, said data structure including a fourth field for holding data indicating an identifier of each unit;
and wherein the indicator comprises the fourth field data.

10. The method of claim 2, wherein the step of receiving, on the processor, further comprises receiving a plurality of admission statuses for the respective plurality of units and wherein said storing further comprises storing the admission status of each unit in the data structure, said data structure including a fifth field for holding data indicating an admission status of each unit;
and wherein the indicator comprises the fifth data field.

11. The method of claim 2, where the step of presenting, on the display, comprises presenting a plurality of indicators in a respective plurality of active areas associated with the respective plurality of units, and wherein the method further comprises:
receiving, on the processor, a signal from the display based on selection of a particular active area of the display; and
presenting, on the display, an image based on second field data from the unit associated with the particular active area.

12. The method of claim 1, wherein the step of determining whether the time gap exceeds the at least one time gap threshold includes determining that the time gap for every unit exceeds the at least one time gap threshold and wherein the remedial action comprises generating an alert including an indication that the at least one server is offline.

13. The method of claim 12, wherein the step of generating the alert comprises transmitting a communication message indicating that the at least one server is offline.

14. The method of claim 1, wherein:
the at least one server comprises a first server and a second server;
the step of storing comprises storing first subject condition data and the current sample time from the first server in a first data structure and storing second subject condition data and the current sample time from the second server in a second data structure.

15. The method of claim 14, wherein:
the step of determining whether the time gap exceeds the at least one time gap threshold includes determining that a time gap based on the first data structure for a first unit exceeds the at least one time gap threshold and determining that a time gap based on the first data structure for a second unit is less than the at least one time gap threshold and determining that a time gap based on the second data structure for the first unit is less than the at least one time gap threshold;
and the remedial action comprises generating an alert including an indication of a disconnection between the first server and a first subject condition data monitor associated with the first unit.

16. The method of claim 15, wherein the generating the alert comprises transmitting a communication message indicating the disconnection between the first server and the first subject condition data monitor.

17. The method of claim 14, wherein:
the step of determining whether the time gap exceeds the at least one time gap threshold includes determining that the time gaps based on the first data structure and second data structure each exceed the at least one time gap threshold for a first unit and that the time gaps based on the first data structure and second data structure are each less than the least one time gap threshold for a second unit;
and the step of remedial action comprises generating an alert including an indication of a disconnection between a first subject condition data monitor associated with the first unit and the first and second servers.

18. The method of claim 17, wherein the step of generating the alert comprises transmitting a communication message indicating the disconnection of the first subject condition data monitor from the first and second servers.

19. The method of claim 1, wherein the remedial action comprises transmitting an alert message to a workstation at the facility, said communication message identifying at least one unit where the time gap exceeds the at least one time gap threshold.

20. A non-transitory computer-readable medium for storing a sequence of instructions and a data structure including two or more records, wherein each record includes two or more fields, wherein execution of the one or more sequences of instructions by one or more processors causes the one or more processors to perform the steps of:
receiving a value of at least one parameter of subject condition data and a value of a sample time from at least one server at each of a plurality of sample times, where the value of the at least one parameter and the value of each sample time is received on the at least one server from a plurality of subject condition data monitors associated with a respective plurality of units in a facility;
storing the subject condition data from each unit in one of the records of the data structure at a current sample time, wherein the two or more fields include a first field for holding data indicating the current sample time and a second field for holding data indicating a value of the at least one parameter of the subject condition data;
determining a time gap defined by a duration between the current sample time and a most recent sample time;
determining whether the time gap for each unit exceeds at least one time gap threshold; and
causing an apparatus to perform a remedial action based on the determining whether the time gap exceeds the at least one time gap threshold.

21. An apparatus comprising:
at least one processor; and
at least one memory including one or more sequences of instructions and a data structure including two or more records, wherein each record includes two or more fields, the at least one memory and the one or more sequences of instructions configured to, with the at least one processor, cause the apparatus to perform at least the following:
receive a value of at least one parameter of subject condition data and a value of a sample time from at least one server at each of a plurality of sample times, wherein the at least one server is configured to receive the value of the at least one parameter of subject condition data and the value of the sample time from a plurality of subject condition data monitors associated with a respective plurality of units in a facility;
store the subject condition data from each unit in one of the records of the data structure at a current sample time, wherein the two or more fields include a first field for holding data indicating the current sample time and a second field for holding data indicating a value of the at least one parameter of subject condition data;
determine a time gap defined by a duration between the current sample time and a most recent sample time;
determine whether the time gap for each unit exceeds at least one time gap threshold; and
cause a secondary apparatus to perform a remedial action based on the determination of whether the time gap exceeds the at least one time gap threshold.

22. The apparatus of claim 21, wherein the secondary apparatus is a display and wherein the remedial action comprises presenting an alert including an indicator for each unit on the display.

23. The apparatus of claim 22, wherein the indicator is a color-coded indicator.

24. The apparatus of claim 21, further comprising:
the plurality of subject condition data monitors; and
the at least one server.

* * * * *